(12) United States Patent
Tai et al.

(10) Patent No.: US 11,291,377 B2
(45) Date of Patent: Apr. 5, 2022

(54) BIOCOMPATIBLE PACKAGING FOR LONG TERM IMPLANTABLE SENSORS AND ELECTRONICS

(71) Applicant: California Institute of Technology, Pasadena, CA (US)

(72) Inventors: Yu-Chong Tai, Pasadena, CA (US); Yang Liu, Pasadena, CA (US); Aubrey M. Shapero, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 501 days.

(21) Appl. No.: 15/076,184

(22) Filed: Mar. 21, 2016

(65) Prior Publication Data

US 2016/0287101 A1    Oct. 6, 2016

Related U.S. Application Data

(60) Provisional application No. 62/140,571, filed on Mar. 31, 2015.

(51) Int. Cl.
*A61B 5/03* (2006.01)
*A61B 5/0215* (2006.01)
(Continued)

(52) U.S. Cl.
CPC ........ *A61B 5/02156* (2013.01); *A61B 5/0215* (2013.01); *A61B 5/02141* (2013.01);
(Continued)

(58) Field of Classification Search
CPC ...... A61B 5/03–038; A61B 2562/0247; A61B 2562/028; A61B 2562/0285; G01L 19/0046; G01L 19/0645
(Continued)

(56) References Cited

U.S. PATENT DOCUMENTS 3,341,794 A      9/1967  Stedman
3,838,684 A  *  10/1974  Manuel  ............. A61B 5/02438
                                                      361/283.4
(Continued)

FOREIGN PATENT DOCUMENTS

CN         2366109 Y      3/2000
CN       101032400 A      9/2007
(Continued)

OTHER PUBLICATIONS

Wacker Silicone Oil. 2002.*
(Continued)

*Primary Examiner* — David J. McCrosky
(74) *Attorney, Agent, or Firm* — Kilpatrick Townsend & Stockton LLP

(57) ABSTRACT

An implantable medical device is described. In an example, the implantable medical device includes an electromechanical substrate and sensor, such as a pressure sensor, disposed on the substrate. At least a portion of the sensor is packaged via a liquid encapsulation. The packaging includes a shaped flexible outer membrane that surrounds at least the portion of the sensor. The packaging also includes a hydrophobic liquid disposed between at least the portion of the pressure sensor and the flexible outer membrane. The implantable medical device can be a part of a medical system used for monitoring medical conditions or performing medical operations based on the implantable medical device. Additionally, manufacturing methods are described for packaging the sensor in a liquid encapsulation.

18 Claims, 13 Drawing Sheets

(51) Int. Cl.
  *G01L 9/00* (2006.01)
  *A61B 5/021* (2006.01)
(52) U.S. Cl.
  CPC .................. *A61B 5/03* (2013.01); *G01L 9/00* (2013.01); *A61B 2562/0247* (2013.01); *A61B 2562/12* (2013.01); *A61B 2562/162* (2013.01); *A61B 2562/168* (2013.01)
(58) Field of Classification Search
  USPC ............................................ 73/731; 600/561
  See application file for complete search history.

(56) References Cited

U.S. PATENT DOCUMENTS

| | | | |
|---|---|---|---|
| 4,264,889 A * | 4/1981 | Yamamoto | G01L 13/025 338/3 |
| 4,519,401 A | 5/1985 | Ko | |
| 4,586,018 A * | 4/1986 | Bettman | G01L 19/0645 338/2 |
| 4,604,900 A | 8/1986 | Knudsen et al. | |
| 4,662,226 A | 5/1987 | Wang | |
| 4,846,191 A | 7/1989 | Brockway et al. | |
| 5,535,752 A | 7/1996 | Halperin et al. | |
| 6,010,461 A | 1/2000 | Haniff et al. | |
| 6,134,970 A * | 10/2000 | Kumakawa | G01L 1/205 600/595 |
| 6,148,673 A | 11/2000 | Brown | |
| 6,221,024 B1 | 4/2001 | Miesel | |
| 6,439,055 B1 | 8/2002 | Maron et al. | |
| 8,313,811 B2 | 11/2012 | Hogg et al. | |
| 8,313,819 B2 | 11/2012 | Hogg et al. | |
| 8,361,591 B2 | 1/2013 | Hogg et al. | |
| 8,529,538 B2 | 9/2013 | Pang et al. | |
| 8,603,024 B2 | 12/2013 | Bohm et al. | |
| 8,764,685 B2 * | 7/2014 | Casey | A61B 17/135 600/485 |
| 8,926,510 B2 | 1/2015 | Marshall et al. | |
| 2002/0073783 A1 | 6/2002 | Wilner | |
| 2004/0020300 A1* | 2/2004 | Boehler | G01L 19/04 73/708 |
| 2004/0073122 A1 | 4/2004 | Stofer | |
| 2004/0162545 A1 | 8/2004 | Brown et al. | |
| 2004/0176672 A1 | 9/2004 | Silver et al. | |
| 2005/0288596 A1 | 12/2005 | Eigler et al. | |
| 2006/0071286 A1 | 4/2006 | Axelrod et al. | |
| 2006/0189887 A1 | 8/2006 | Hassler, Jr. et al. | |
| 2006/0189917 A1 | 8/2006 | Mayr et al. | |
| 2006/0211914 A1 | 9/2006 | Hassler, Jr. et al. | |
| 2007/0118038 A1 | 5/2007 | Bödecker et al. | |
| 2007/0243230 A1 | 10/2007 | de Juan, Jr. et al. | |
| 2008/0139959 A1 | 6/2008 | Miethke et al. | |
| 2010/0312188 A1 | 12/2010 | Robertson et al. | |
| 2011/0045509 A1 | 2/2011 | Melchers | |
| 2011/0066046 A1 | 3/2011 | Young et al. | |
| 2011/0071454 A1 | 3/2011 | Dos Santos et al. | |
| 2011/0071456 A1 | 3/2011 | Rickard | |
| 2011/0071458 A1 | 3/2011 | Rickard | |
| 2011/0071459 A1 | 3/2011 | Rickard et al. | |
| 2011/0132097 A1 | 6/2011 | Hegner et al. | |
| 2011/0160560 A1 | 6/2011 | Stone | |
| 2011/0271764 A1 | 11/2011 | Lee | |
| 2011/0296925 A1 | 12/2011 | Miesel et al. | |
| 2012/0197231 A1 | 8/2012 | Kane et al. | |
| 2012/0247227 A1 | 10/2012 | Crivelli | |
| 2013/0062713 A1 | 3/2013 | Sakuragi et al. | |
| 2013/0137958 A1 | 5/2013 | Tai et al. | |
| 2013/0150776 A1 | 6/2013 | Boehm et al. | |
| 2013/0233086 A1 | 9/2013 | Besling et al. | |
| 2014/0005569 A1* | 1/2014 | Miethke | A61B 5/031 600/561 |
| 2014/0171777 A1 | 6/2014 | Sanchez et al. | |
| 2014/0296687 A1 | 10/2014 | Irazoqui et al. | |
| 2015/0057595 A1 | 2/2015 | Gunn et al. | |
| 2016/0235296 A1 | 8/2016 | Dunning | |
| 2016/0235298 A1 | 8/2016 | Gunn | |
| 2016/0249818 A1 | 9/2016 | Philipp et al. | |
| 2016/0349162 A1 | 12/2016 | Ebert et al. | |
| 2017/0014270 A1 | 1/2017 | Tyler | |
| 2017/0095163 A1 | 4/2017 | Bitzer et al. | |

FOREIGN PATENT DOCUMENTS

| | | | |
|---|---|---|---|
| CN | 200942206 Y | 9/2007 | |
| CN | 101918066 A | 12/2010 | |
| CN | 102202719 | 9/2011 | |
| CN | 203620057 U | 6/2014 | |
| CN | 104010568 | 8/2014 | |
| CN | 205041352 U | 2/2016 | |
| CN | 107529985 | 1/2018 | |
| DE | 102004056757 | 6/2006 | |
| EP | 1312302 A2 * | 5/2003 | ............ A61B 5/031 |
| JP | 2008539811 | 11/2008 | |
| JP | 2010503220 | 1/2010 | |
| JP | 2013545973 | 12/2013 | |
| JP | 2014208301 | 11/2014 | |
| WO | 2005/022110 A2 | 3/2005 | |
| WO | 2008/140395 A1 | 11/2008 | |
| WO | 2011035262 | 3/2011 | |
| WO | 03/094693 A2 | 11/2011 | |
| WO | WO-2013003754 A1 * | 1/2013 | ........... A61B 5/6861 |
| WO | 2014/0005569 A1 | 1/2014 | |
| WO | 2014055989 | 4/2014 | |
| WO | 2014/195372 A1 | 12/2014 | |
| WO | 2016160402 | 10/2016 | |

OTHER PUBLICATIONS

Wheeler, Jason W., et al. "MEMS-based bubble pressure sensor for prosthetic socket interface pressure measurement." Engineering in Medicine and Biology Society, EMBC, 2011 Annual International Conference of the IEEE. IEEE, 2011.*
Cong, Peng, et al. "Implantable blood pressure monitoring of small animal for advanced biological research." Solid-State Sensors, Actuators and Microsystems, 2005. Digest of Technical Papers. Transducers'05. The 13th International Conference on. vol. 2. IEEE, 2005.*
Machine translation of EP 1312302 A2 (Year: 2019).*
EPO search report in foreign counterpart application (Year: 2018).*
Cong, Peng, Wen H. Ko, and Darrin J. Young. "Wireless implantable blood pressure sensing microsystem design for monitoring of small laboratory animals." Sens. Mater 20 (2008): 327-340. (Year: 2008).*
Hogg, A. (2014) "Development and Characterisation of Ultrathin Layer Packaging for Implantable Medical Devices," PhD Thesis, University of Applied Sciences, University of Bern, 219 pages.
Binh-Khiem, "Tensile Film Stress of Parylene Deposited Liquid," Department of Mechano-Informatics, Graduate School of Information Science and Technology, the University of Tokyo, Langmuir Article, 2010, pp. 18771-18775, vol. 26 (24), American Chemical Society.
PCT/US2018/026705, "International Search Report and Written Opinion Received", dated Jun. 18, 2018, 8 pages.
International Search Report and Written Opinion dated Jun. 27, 2016 for International Searching Authority No. PCT/US2016/23454 filed Mar. 21, 2016; 18 pages.
CN201680027137.3, "Office Action", dated Oct. 31, 2019, 10 pages.
CN201680027137.3, "Office Action", dated Jul. 8, 2019, 6 pages.
CN201680027137.3, "Office Action", dated Dec. 4, 2018, 8 pages.
JP2017-551158, "Office Action", dated Dec. 24, 2019, 10 pages.
PCT/US2016/023454, "International Preliminary Report on Patentability", dated Oct. 12, 2017, 15 pages.
PCT/US2018/026705, "International Preliminary Report on Patentability", dated Nov. 21, 2019, 7 pages.
Shapero et al., "Parylene-Oil-Encapsulated Low-Drift Implantable Pressure Sensors", 31st IEEE International Conference on Micro Electro Mechanical Systems, Jan. 21-25, 2018, pp. 47-50.

(56) References Cited

OTHER PUBLICATIONS

EP18798545.2 , "Extended European Search Report", dated Dec. 9, 2020, 5 pages.

* cited by examiner

1300

```
FORM A VOLUME OF HYDROPHOBIC LIQUID AROUND AT LEAST A
PORTION OF A SENSOR
1302
```

```
FORM FLEXIBLE OUTER MEMBRANE
1304
```

```
DEGAS AT LEAST A PORTION OF A SENSOR
1402
```

```
PLACE AT LEAST THE DEGASSED PORTION IN A SOLUTION OF
HYDROPHOBIC LIQUID
1404
```

```
DEPOSIT POLYMER MATERIAL ON A SURFACE OF THE VOLUME OF
THE HYDROPHOBIC LIQUID
1406
```

```
INDUCE A CURVATURE DESIGN
1408
```

FIG. 14

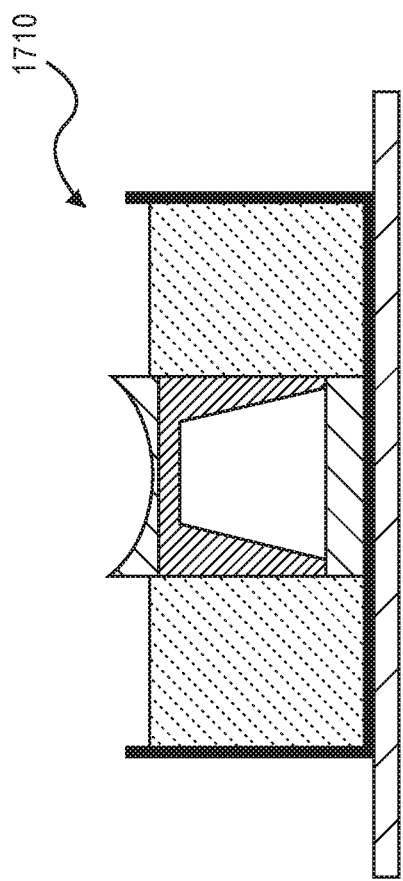
FIG. 17A DEPOSITION TEMPERATURE
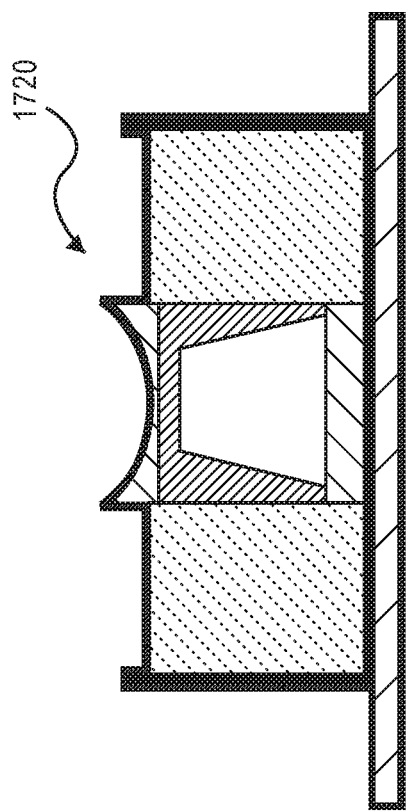
FIG. 17B DEPOSITION TEMPERATURE
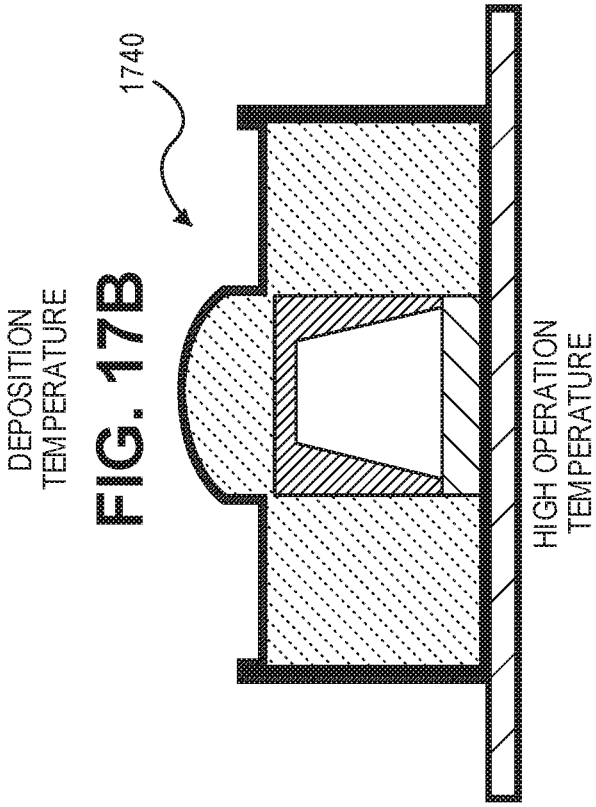
FIG. 17C OPERATION TEMPERATURE
FIG. 17D HIGH OPERATION TEMPERATURE

BIOCOMPATIBLE PACKAGING FOR LONG TERM IMPLANTABLE SENSORS AND ELECTRONICS

CROSS-REFERENCES TO RELATED APPLICATIONS

This application claims the benefit of U.S. Provisional Patent Application No. 62/140,571, filed Mar. 31, 2015, which is hereby incorporated by reference in its entirety for all purposes.

STATEMENT AS TO RIGHTS TO INVENTIONS MADE UNDER FEDERALLY SPONSORED RESEARCH AND DEVELOPMENT

NOT APPLICABLE

BACKGROUND

Implantable medical devices are used for a wide range of medical applications. Some of the applications relate to monitoring medical conditions. Other applications relate to proactively or reactively effectuating particular medical operations.

Generally, an implantable medical device has a small form factor to support implantation in a subject, such as a human patient. In certain medical applications, the implanted medical device resides within an internal environment of the subject (e.g., in proximity of a particular organ within the subject's body) for a period of time. In operation, the implanted medical device is subject to various conditions of the internal environment during the time period. The conditions can affect the short and long term operations of the implanted medical device. For example, agents of the internal environment, such as fluids, can corrode components of the implanted medical device. The corrosion degrades the capability for monitoring a medical condition or effectuation a medical operation.

Packaging of the implantable medical device helps protecting against the conditions of the subject's internal environment. For example, a protective layer encapsulates the implantable medical device to form a package. A variety of materials are available for the encapsulation. A material is deposited on an outer surface of the implantable medical device to form the protective layer. Commonly, the material forms a solid protective layer after the deposition. In certain medical applications, the solidity nonetheless affects the operations of the implantable medical device when implanted in the subject's internal environment.

BRIEF SUMMARY

Generally described is an implantable medical device. In an example, the implantable medical device includes a sensor, such as a pressure sensor. The sensor is configured for implantation in a subject. Once implanted, the sensor is subject to different conditions of the operational environment. To protect against negative effects of these conditions, the sensor is packaged in a liquid encapsulation. The packaging includes a flexible outer membrane that surrounds at least a portion of the sensor. The flexible outer membrane can include corrugations or a cuvature that facilitate expansion and compression. The packaging also includes a hydrophobic liquid disposed between at least the portion of the pressure sensor and the flexible outer membrane.

Generally also described is a manufacturing method for packaging the sensor. The manufacturing method incudes forming a volume of hydrophobic liquid around at least the portion of the sensor. The manufacturing method also includes forming the flexible outer membrane on a free surface of the hydrophobic liquid.

Generally also described is a medical system. The medical system includes the implantable medical device and a computer. Data sensed by the packaged sensor is analyzed by a medical application running on the computer. The medical application facilitates diagnosis of a medical condition, provides control instructions to perform a medical operation, and/or tracks an operational status of the sensor based on the sensed data.

BRIEF DESCRIPTION OF THE DRAWINGS

FIG. 13 is a flowchart with an example method for manufacturing an implantable medical device packaged for protection against conditions of an operation environment, in accordance with an embodiment.

FIG. 14 is a flowchart with an example of a more detailed method for manufacturing an implantable medical device packaged for protection against conditions of an operation environment, in accordance with an embodiment.

FIGS. 17A, 17,B, 17C, and 17D illustrate an example of octadecane-based shaping of a surface curvature, in accordance with an embodiment.

DETAILED DESCRIPTION

Figure 1:
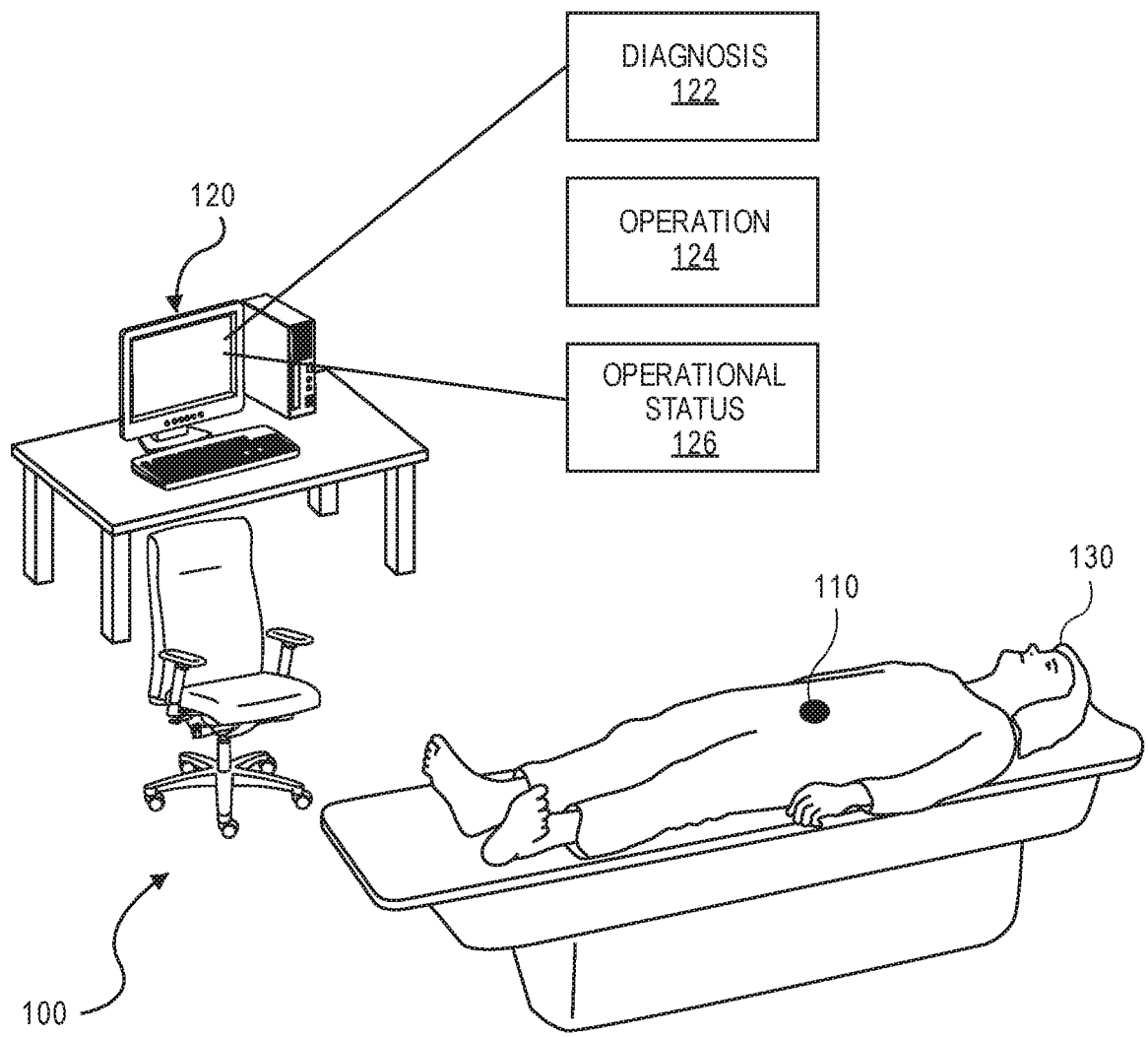
FIG. 1 illustrates an example medical system that uses an implantable medical device, in accordance with an embodiment.

Specific details of various exemplary embodiments of the present invention are set forth in the following description and are illustrated in the figures. Certain well-known technology details, such as methods, apparatus, or systems that would be known by one of ordinary skill, are not set forth in the following description or in the figures to avoid unnecessarily obscuring the various examples. Those of ordinary skill in the relevant art will understand that they can practice other examples of the disclosed subject matter without departing from the scope and spirit of the present invention.

Embodiments for packaging an implantable medical device are described. Embodiments for methods of manufacturing such a packaged, implantable medical device are described. In addition, embodiments for a medical system that includes a packaged, implantable medical device are described.

Generally, an implantable medical device represents a medical device suitable for or capable of being implanted in an operational environment, such as within a subject (e.g., a human patient). Once implanted, the implanted medical device provides one or more medical operations relative to the operational environment. For ease of reference, an "implantable medical device" and an "implanted medical device" are referred to herein as a "medical device." Whether the medical device is implanted or is implantable depends on whether the medical device has or has not been implanted, respectively, in the operational environment. As such, the medical device refers to the implantable medical device if the medical device is not implanted. The medical device also refers to the implanted medical device if the medical device is implanted.

Described herein are packaging of the medical device for long term operation within the operational environment. On one hand, the packaging reduces negative (e.g., harmful) effects on the medical device from the conditions of the operational environment. On the other hand, the packaging also maintains the proper operations of the medical device (e.g., does not substantially degrade the capability(ies) of the medical device).

In an example, the medical device includes an operational component (e.g., a sensor) that should be protected against the conditions of the operational environment. The operational component provides one or more of the operations of the medical device relative to the operational environment. To do so, a packaging is formed around at least the operational component. The packaging is, for instance, biocompatible and hermetic and includes a hydrophobic liquid and outer membrane. The hydrophobic liquid surrounds at least the operational component and includes, for instance, an oil such as a silicone oil or a vegetable oil. In turn, the outer membrane surrounds a free surface of the hydrophobic liquid and is non-porous and flexible. For instance, the outer membrane uses a polymer material such as silicone, poly (p-xylylene) (e.g., parylene-C or D), polyimide, or a thin metal.

Because the outer membrane is non-porous and because the liquid is hydrophobic, exposure of the operational component to harmful agents of the operational environment (e.g., fluids such as water) is reduced. For example, direct contact is delayed or substantially eliminated for a period of time. Hence, the packaging protects the operations component from the negative effects of the conditions of the operational environment.

Because the outer membrane is flexible and liquid is used, proper operations of the medical device are maintained. For example, the operational component includes a pressure sensor. The difference between the pressure within the package and the pressure on the outside of the package is substantially negligible because of the flexible packaging. The pressure differential, if any, does not overly affect the sensitivity of the pressure sensor to sense the pressure outside of the package. Hence, the packaging does not degrade the capability of the medical device with respect to pressure sensing.

FIG. 1 illustrates an example medical system 100 that supports multiple medical applications. For example, the medical system 100 monitors medical conditions. The monitoring includes collecting medical data related to an operational environment, such as medical data related to a medical condition of a patient. The monitoring also includes analyzing the medical data to diagnose the medical condition. In another example, the medical system 100 effectuates a medical operation to help with or against the medical condition.

Generally, the medical system 100 includes a medical device 110 and a computer 120. The medical device 110 includes various components. Some of the components can be implanted in a subject 130, such as a human patient. Such components collect medical data from an operational environmental within which the components are implanted and/or effectuate medical operations in the operational environment. For example, the implantable components include any of sensors, actuators, electrical components, electronic components, mechanical components, and substrates carrying such components. Other components are not necessarily implanted in the subject 130. Such components support the operations of the implanted components. For example, the non-implantable components provide an interface between the implantable components and the computer 120, power to some of the implantable components, and/or an operator interface to an operator of the medical system 100 (e.g., a doctor operating on the subject 130). The interface to the computer 120 supports transmission of data from the implantable components to the computer 120 and/or control over the operations of the implantable components from the computer 120. Example of the non-implantable components include a wired and/or wireless data port, a power source, a power port, data wires, power wires, a handle, and/or a catheter.

In certain medical applications, the medical device 110 is implanted in the subject 130 for a period of time and is subject to the operational environment during that period of time. The length of the period of time depends on the medical application and can vary between a day to months and even years. Proper operations of the medical device 110 within the period of time is desired. Packaging the medical device 110 supports the proper operations. As further illustrated in the next figures, the packaging can protect at least some or all of the implantable components. In turn, protecting an implantable component includes packaging a portion or the entire implantable component.

The computer 120 represents a head end that analyzes medical-related data and/or controls medical-related operations. In an example, the computer 120 includes a memory, a processor, and user input/output devices (e.g., a display, keyboard, mouse, etc.). Data collected by the medical device 110 is provided to the memory. Any suitable memory can be used such as RAM and/or ROM memories. The memory hosts a medical application that is executed by the processor. Any suitable processor can be used such as a general central processing unit (CPU). A user interface (UI) is available on one of the input/output devices (e.g., the display) to interface with the medical application. Any suitable display, of any suitable size and/or type, can be used to provide the UI. The UI enables the operator of the medical system 100 to interface with the medical application.

The medical application provides various medical-related functionalities. For example, the medical application facilitates medical diagnosis 122 based on data collected by the medical device 110, directs medical operations 124 through the medical device 110, and/or identifies an operational status 126 of the medical device 110.

In an example, the medical diagnosis 122 identifies a medical condition of the subject 130. The medical application stores correlations between medical data and medical conditions. Based on the data collected by the medical device 110 (e.g., sensed data from an implanted sensor), the medical application identifies the medical condition from the correlations. The medical application outputs the medical condition as part of the medical diagnosis 122 on the UI of the computer 120. In addition, the medical application stores calibration data for the medical device 110. The calibration data is used to adjust the collected data such that the medical diagnosis 122 is generated from the adjusted data. For instance, the calibration data is specific to a sensor of the medical device 110. In this case, the calibration data depends on the sensor and the packaging that protects the sensor (e.g., any flexible outer membrane and hydrophobic liquid that form the package). The calibration data can be developed through testing in a developmental environment and provided from a manufacturer of the medical device 110.

In an example, the medical operations 124 control operations of some or all of the components of the medical device 110. The medical application stores control instructions or provides controls over such operations to the operator via the UI. The control can be in response to the medical diagnosis 122. For instance, the medical application stores correlations between medical conditions and operations to be performed. As such, the medical application automatically selects a particular set of control instructions, recommends an operation to the operator via the UI, and/or receives control instructions from the operator via the UI. The control instructions are transmitted from the computer 120 to the medical device 110, thereby effectuating the desired operation. For instance, a sensor of the medical device 110 can be repositioned to another location within the subject 110 and/or can increase a rate at which data is sensed.

In an example, operational status 126 identifies whether the medical device 110 is properly operating in the operational environment. The operation status 126 can be specific to a particular component of the medical device 110 (e.g., to a particular sensor) or can represent an overall status. For instance, the medical application stores a period of time that identifies an operation life of a sensor. The medical application detects that the operation life has expired based on the date of implantation and the period of time. In this case, the medical application displays an operational status on the UI that the sensor has become defective. In another illustration, the medical application tracks the change in the data collected by the sensor. If the change has a slope that exceeds a threshold (e.g., the change is a relatively significant step change), the medical application displays that the sensor has become defective. That is because the amount of change indicates a failure in properly sensing the data.

Hence, the medical device 110 can be implanted in the subject 130. The computer 120 in communication with the medical device 110 can provide diagnosis of a medical condition of the subject 130, operational controls over the medical device 110 while implanted in the subject 130, and operational status of the medical device 110. The proper operations of the medical device 110 while implanted in the subject 130 for a period of time depends on the packaging that protects the medical device 110 from conditions of the operational environment.

In an illustration, consider an example where the medical device 110 includes a pressure sensor. In this example, the medical device 110 is implanted in the subject 130 for continuous internal body fluid pressure monitoring in organs such as the heart, eye, brain, and/or bladder. The monitoring is used to diagnose health or progression of disease. Disease examples include restenosis, hypertension, heart failure, glaucoma, intracranial hypertension, and urinary incontinence. The monitoring can extend over a long term, such as over a year time period. Although telemetric techniques exist for some applications, none provides adequate precision and accuracy for that long time period unless the pressure sensor is properly packaged. For instance, other than the CardioMEMS® sensor, no pressure sensor is known to have lasted operationally more than one month inside the body due to a variety of reasons ranging from electronics failure to sensitivity and offset drift. Both kinds of drift are caused by the accumulation of biological material on the surface of the pressure sensor which changes the mechanical properties of the pressure membrane.

Described herein is packaging of the medical device 110 where the packaging maintains the accuracy of the pressure sensor (and, similarly, other components of the medical device 110) for as long as possible in the operational environment. The packaging protects the sensor's pressure membrane and some of the medical device's 110 circuitry from the operational environment. Hence, such components are not in direct contact with bodily fluids. However, the packaging is flexible such that the pressure membrane can properly deflect to sense the environmental pressure.

In an example, the packaging protects the pressure sensor and the circuitry with silicone oil of about 100,000 centistokes (cSt) ($10^{-1}$ $m^2/s$) kinematic viscosity and a parylene-D outer membrane of about a 24.92 μm (about $9.8 \times 10^{-4}$ inches) in thickness. Experimentally, this packaging shows good performance for six weeks in 77° C. (170.6° F.) saline with more than 99% of the original sensor sensitivity. This experimental lifetime corresponds to a predicted lifetime of around twenty-one months in 37° C. (98.6° F.) saline according to the Arrhenius equation with an activation energy of −0.6 eV (−$9.6 \times 10^{-20}$ J). Accordingly, with proper designs, the packaging can preserve the original pressure sensor sensitivity without offset.

Figure 2:
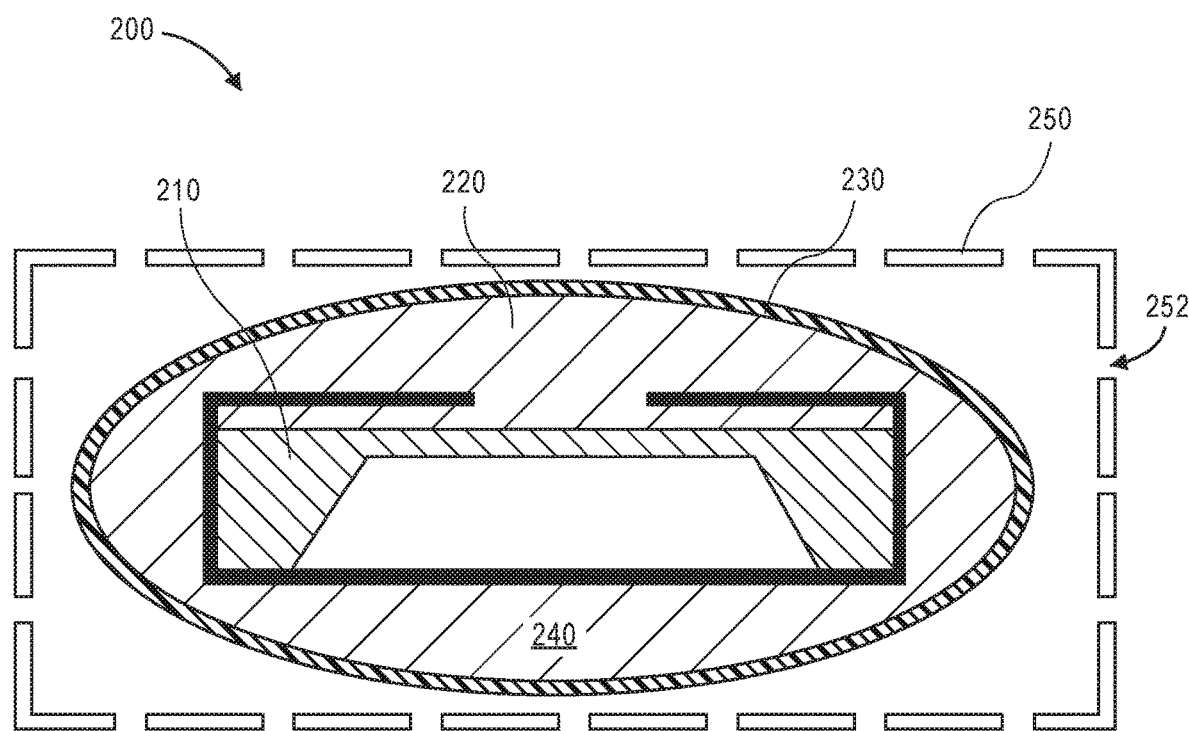
FIG. 2 illustrates an example implantable medical device packaged for protection against conditions of an operational environment, where the packaging uses a hydrophobic liquid and an outer membrane, in accordance with an embodiment.

FIG. 2 illustrates an example of a packaged medical device 200 with a pressure sensor 210, such as the pressure sensor of the medical device 110. The packaging can be similarly applied to other components of a medical device including, for example, other types of sensors (e.g., ultrasound sensor, light sensor), actuators, electrical components, electronic components, mechanical components, and substrates carrying such components. Generally, the packaging represents a hermetic biocompatible package that protects a respective component(s) from conditions of an operational environment. This package blocks agents in the operational environment (e.g., contaminants within a body of a subject) from reaching the respective component(s) while still enabling the proper operations of respective component(s). Thereby, the packaging is suitable for long term implantation of the respective component(s).

As illustrated, the pressure sensor 210 (and other related electronics) are packaged using liquid encapsulation. The liquid encapsulation includes a volume 220 of liquid 240 that surrounds the pressure sensor 210 and an outer membrane 230 that surrounds the volume 220.

In an example, the liquid is a benign, biocompatible liquid that blocks corrosive agents of the operational environment from direct contact with the pressure sensor 210 (and the protected electronics). For instance, the liquid includes a hydrophobic liquid, such as a biocompatible oil (e.g., a silicone oil or a vegetable oil), that repels water and, thus, the acidic and basic components in water that causes corrosion. Repelling the corrosive agents prevents corrosion from causing failure in long-term implants. The liquid also protects the pressure sensor (and the protected electronics) against coating and biological encapsulation from the operational environment. Coating and subsequent biologic encapsulation will appear, instead, on the package and, thus, will minimally affect proper operations or sensitivity of the pressure sensor (and the protected electronics).

In an example, the outer membrane 230 is a non-porous, flexible membrane made out of a biocompatible polymer material, such as silicone, parylene-C, parylene-D, a polyimide, and/or a thin metal. The outer membrane 230 is highly flexible and/or deformable so that mechanical and electronic components of the pressure sensor 210 are separated from biologic compounds that typically surround implants. Because tissues in biological fouling have low Young's modulus, the outer membrane 230 will deform even after biological coating.

The volume 220 of liquid and the outer membrane 230 do not create a substantial pressure differential between the inside and the outside of the package. Thus, the proper functionality is maintained for any mechanical transducing elements of the pressure sensor 210. For example, about a zero pressure difference across the outer membrane 230 means that the pressure within the volume 220 is substantially equal to the pressure outside the outer membrane 230. In this way, packaging is "invisible" to the pressure sensor 210 during operation, yet protects the pressure sensor 210 for long-term implantation.

The flexibility of the packaging is effectuated by a choice of materials and/or geometric design. For example, silicone oil of kinematic viscosity selected from a kinematic viscosity range of 0.45 to 100,000 cSt ($45 \times 10^{-8}$ to $10^{-1}$ m$^2$/s) is used in the volume 220. Silicone, parylene-C, parylene-D, a polyimide, and/or a thin metal is deposited on the outer, free surface of the volume 220 to form a non-porous, flexible membrane (e.g., the outer membrane) of a thickness that varies between 1 to 100 µm ($3.9 \times 10^{-5}$ to $3 \times 10^{-3}$ inches). In addition, the curvature of the outer membrane 230 can be designed to maintain the pressure functionality of the pressure sensor 210 by substantially reducing or eliminating the pressure differential. Examples of curvature designs are further described in connection with FIGS. 7, 8, and 9.

In an example, the packaging also includes a rigid assemblage, such as a protective cage 250. The rigid assemblage represents a rigid structure made out a biocompatible metal alloy and/or a polymer. The alloy and/or polymer can be corrosion resistant and/or protected against corrosion using silicone, parylene-C, parylene-D, a polyimide, and/or a thin metal. Different configurations of the rigid assemblage 250 are possible. One example configuration is an outer configuration. In this example, the rigid assemblage 250 contains the pressure sensor 210, volume 220 of liquid 240, and the outer membrane 230. Another example configuration is an inner configuration. In this example, the rigid assemblage 250 is disposed within the volume 220 and contains the pressure sensor 210 (or surrounds a portion of the pressure sensor 210 such as the pressure membrane). In both illustrations, an outer surface of the rigid assemblage 250 includes holes 252. The holes allow the flow of liquid and, thereby, avoid impacting the functionality of the pressure sensor 210. The size of the holes 252 depends on the configuration. Generally, the holes 252 of the outer configuration are smaller than the holes 252 of the inner configuration because of the kinematic viscosity of the liquid within the volume 220.

Figure 3:
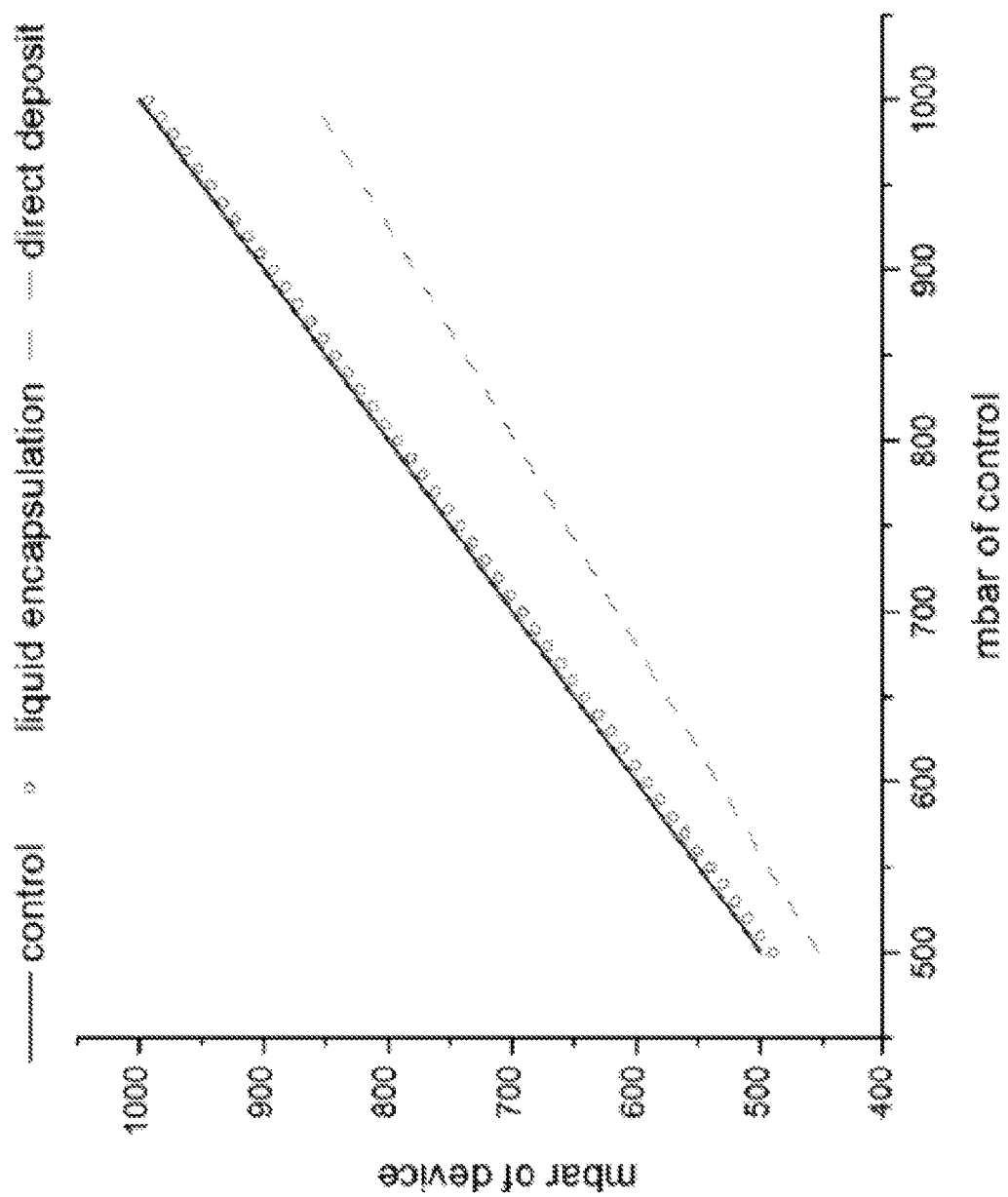
FIG. 3 is a chart comparing performances of packaged and unpackaged implantable pressure sensors, in accordance with an embodiment.

FIG. 3 is a chart of experimental results for three medical devices. Each of the medical devices include a pressure sensor. The pressure sensor of one of the medical devices, referred to as a control device, was not protected. A pressure sensor of a second medical is protected with a liquid encapsulation package as described in connection with FIG. 2. The liquid encapsulation package uses silicone oil of about a 20 cSt ($2 \times 10^{-5}$ m$^2$/s) kinematic viscosity oil and a parylene-C outer membrane of about a 7.81 µm (about $3.1 \times 10^{-4}$ inches) thickness. A pressure sensor of a third medical device is protected with an alternative package. The alternative package does not use any liquid volume. Instead, parylene-C is directly deposited on the pressure sensor to form a protective layer of about 7.81 µm (about $3.1 \times 10^{-4}$ inches). The performance of a medical device represents a relative sensitivity of a pressure sensor to pressure. The relative sensitivity is assessed against the sensitivity of the control device. The three medical devices were subject to a range of pressure. The sensed pressures were collected.

As illustrated, the pressure that the control device sensed is illustrated on the horizontal axis. That pressure varied between 500 and 1000 mbar (7.25 to 14.5 pound-force per square inch-psi). The pressure sensed by each control device is illustrated on the vertical axis. As illustrated, the relative sensitivity of the control device is "1" and is shown with a solid line. In comparison, the relative sensitivity of the second medical device (the one using liquid encapsulation) is substantially the same as the relative sensitivity of the control device (about 1.0055), as shown with a dotted line that substantially overlaps the solid line. In particular, the offset from the control device is about −10.0771 mbar (−0.146 psi) at 500 mbar (7.25 psi) and averages −8.70 mbar (−0.1262 psi). The relative sensitivity of the third medical device (the one using direct depositions) is about 0.8152, as shown with a dashed line that has an offset from the solid line. In particular, the offset from the control device is about −46.76 mbar (−0.68 psi) at 500 mbar (7.25 psi) and averages −92.96 mbar (−1.34 psi).

Hence, lab experiments show that the performance of a pressure sensor protected with liquid encapsulation does not substantially degrade. Other encapsulation methods, such as direct deposit of a protective layer on a pressure sensor, can substantially degrade the performance.

Figure 4:
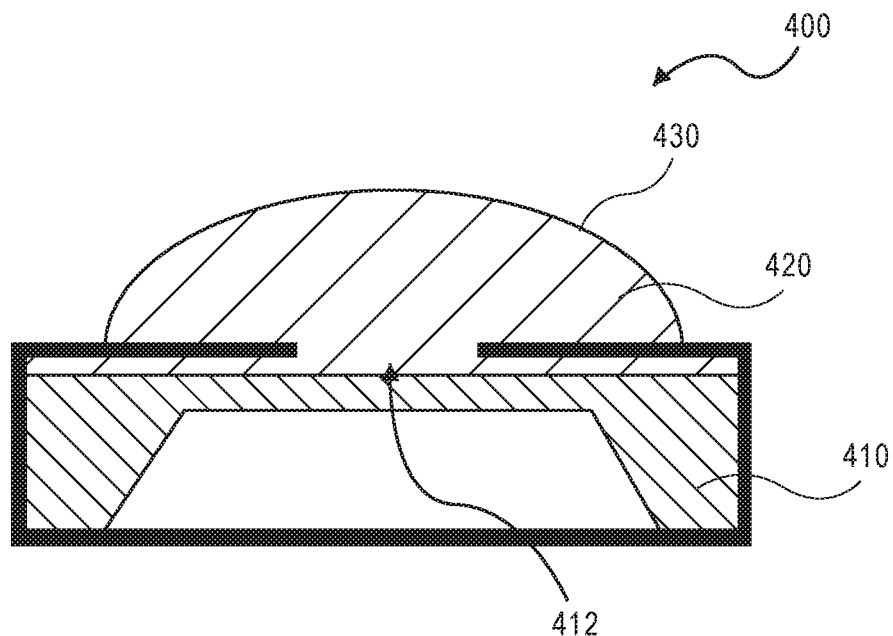
FIG. 4 illustrates an example of packaging a portion of an implantable medical device, in accordance with an embodiment.

FIG. 4 illustrates another example of packaging that uses liquid encapsulation. Whereas the example of FIG. 2 illustrates an entire encapsulation of a pressure sensor, the example of FIG. 4 illustrates a liquid encapsulation system 400 of a portion of a pressure sensor 410. This partial liquid encapsulation system 400 can be similarly applied to other types of sensors or implantable components of a medical device.

As illustrated, the pressure sensor 410 includes a pressure port 412, such as an orifice through an outer surface of the pressure sensor 410. A pressure membrane is located around, adjacent to, in proximity of, or within the pressure port 412. As such, the pressure port 412 allows a mechanical deformation of the pressure membrane. The mechanical deformation is proportional to the environmental pressure around the pressure port 412. The pressure sensor 410 senses this pressure from the mechanical deformation.

In an example, the partial liquid encapsulation 400 involves forming a protective package around only a portion of the pressure sensor. The portion contains the pressure port 412. Hence, a volume 420 of liquid, such as a hydrophobic liquid, surrounds the pressure port 412 and other areas of the pressure sensor 410 that the liquid fills through the pressure port 412. For instance, the liquid is deposited on the pressure sensor 410 around the pressure port 412 or, conversely, the pressure sensor 410 is dipped in the liquid around the pressure port 412 to form the volume. A non-porous, flexible outer membrane 430 is formed around a free surface of the volume 420. For instance, silicone, parylene-C, parylene-D, a polyimide, and/or a thin metal is deposited over the volume 420 to form the outer membrane 430.

Remaining portions of the pressure sensor 410, such as the portions not protected with the partial liquid encapsulation 400, need not but can also be protected. In an example, similar liquid encapsulations are separately applied to the remaining portions. In another example, a protective layer is directly deposited on the remaining portions. For instance, the protective layer is formed using silicone, parylene-C, parylene-D, a polyimide, and/or a thin metal.

Figure 5:
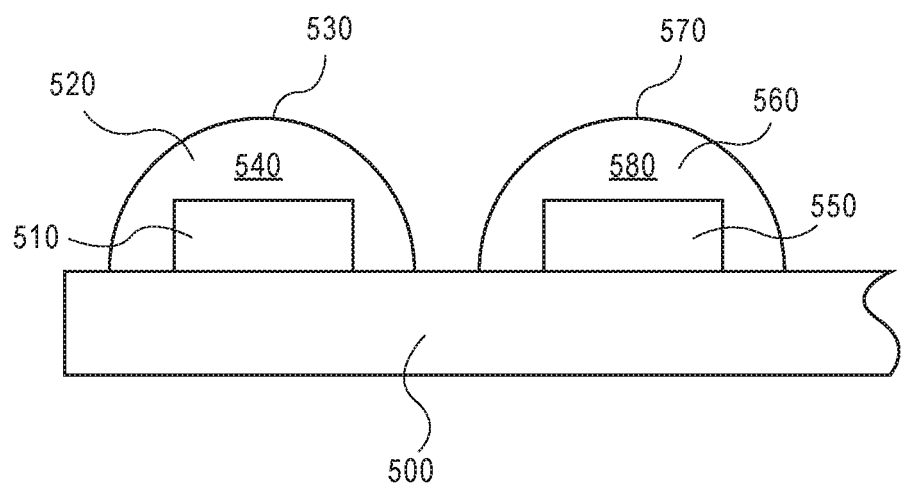
FIG. 5 illustrates an example of packaging multiple portions of an implantable medical device, in accordance with an embodiment.

FIG. 5 illustrates an example medical device assembly 500 that includes multiple implantable components. Generally, full liquid encapsulation, as illustrated in FIG. 2, or partial liquid encapsulation as illustrated in FIG. 4 can be applied separately to each of the implantable components. Alternatively or additionally, liquid encapsulation can also be applied collectively to two or more implantable components such that this single liquid encapsulation protects the two or more implantable components.

As illustrated, the medical device assembly 500 includes a pressure sensor 510 and an ultrasound sensor 550. Other types of sensors and implantable components can be similarly used and protected. In an example, liquid encapsulation is applied to the pressure sensor 510. This liquid encapsulation includes a volume 520 of liquid 540, such as a hydrophobic liquid, that surrounds the pressure sensor 510 fully or partially. The liquid encapsulation also includes an outer membrane 530, such as one formed by silicone, parylene-C, parylene-D, a polyimide, and/or a thin metal around a free surface of the volume 520.

The ultrasound sensor 550 can be similarly packaged by using a separate liquid encapsulation. For example, a volume 560 of liquid 580, such as a hydrophobic liquid, surrounds the ultrasound sensor 550 fully or partially. An outer membrane 570 is formed using silicone, parylene-C, parylene-D a polyimide, and/or a thin metal around a free surface of the volume 560.

The volumes, sizes, geometric shapes, types of materials, viscosities of liquid, and/or other properties of the liquid encapsulations need not but can be the same across the two liquid encapsulations. For example, an optimal kinematic viscosity of liquid and an optimal thickness of the outer membrane can be applied to form a liquid encapsulation dependent on the functionality of the respective sensor. Generally, the optimality represents a certain value that minimizes or reduces to an acceptable threshold the impact of the liquid encapsulation on the proper functionality of the respective sensor.

Figure 6:
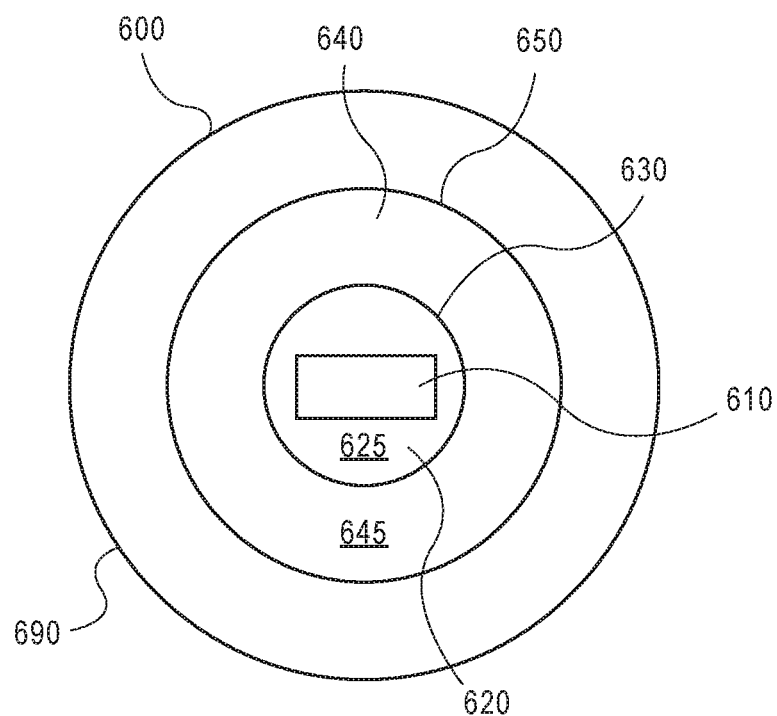
FIG. 6 illustrates an example of a multi-layer package of an implantable medical device, in accordance with an embodiment.

FIG. 6 illustrate a multiple layer liquid encapsulation of an implantable component 610 of a medical device. For example, the implantable component 610 includes a pressure sensor (and/or similarly other sensor types, electrical, electronic, or mechanical components) disposed on a substrate and associated circuitry. Generally, the multiple layer liquid encapsulation includes an inner liquid encapsulation nested in another liquid encapsulation and so on and so forth up to an outer liquid encapsulation layer.

As illustrated, a first liquid encapsulation layer is formed by a volume 620 of liquid 625 and an outer membrane 630. The volume 620 contains the implantable component 610, fully or partially. The outer membrane 630 is formed on a free outer surface of the volume 620.

A second liquid encapsulation layer is formed around the first liquid encapsulation layer, fully or partially. For example, the second liquid encapsulation layer includes a volume 640 of liquid 645 and an outer membrane 650. The volume 640 has an inner perimeter defined by the outer membrane 630 of the first liquid encapsulation layer. The volume 640 also has an outer perimeter defined by the outer membrane 650 of the second liquid encapsulation layer. Liquid 645 of the second liquid encapsulation layer is disposed between the inner and outer perimeters. Hence, when the two nested liquid encapsulation layers are viewed together as a whole, the outer membrane 630 represents an inner membrane that separates the two volumes 620 and 640. This nesting of liquid encapsulation layers can be repeated up to an outer membrane 690.

Although FIG. 6 illustrates concentric spherical layers, other types of layering and geometry are likewise applicable. For instance, each layer can have a particular geometric shape and center that differs from those of another layer. In addition, the volumes need not, but can be the same. Similarly, the liquids need not but can be same. The thicknesses and/or materials for the outer membranes need not, but can also be the same. In an example, a different hydrophobic liquid or kinematic viscosity of such a liquid and a different material-based outer membrane is used for each layer. The layer diversity allows each layer to be designed for protecting the implantable component 610 from particular conditions of an operational environment. For instance, the first liquid encapsulation layer protects against acidic agents, whereas the second liquid encapsulation layer protects against basic agents of the operational environment.

Figure 7:
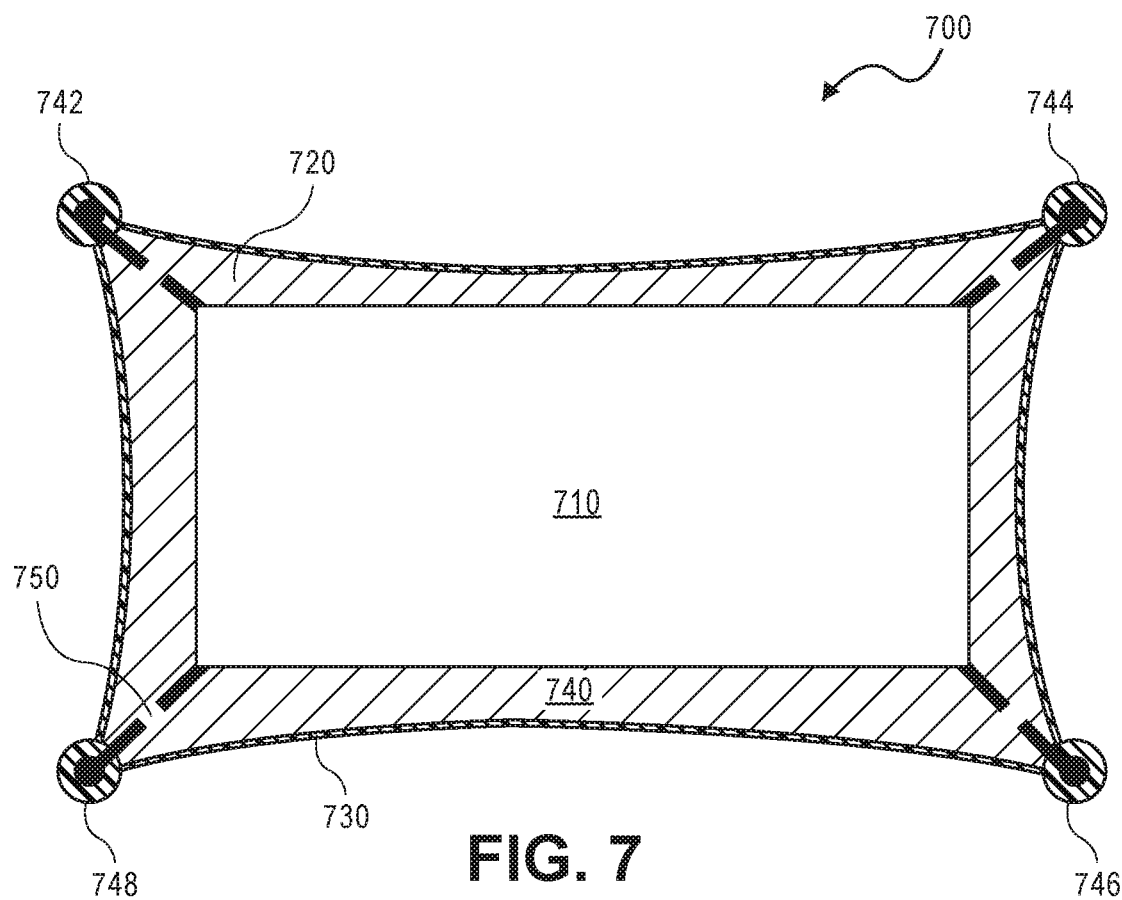
FIG. 7 illustrates an example surface configuration of a package, in accordance with an embodiment.

FIG. 7 illustrates an example surface configuration of a package assembly 700 that includes liquid encapsulation. Although a pressure sensor 710 is described in connection with the illustrated surface configuration, the package similarly protects other types of sensors and/or implantable components of a medical device.

Generally, the package protects the pressure sensor against long term exposure to conditions of an operational environment, thereby avoiding sensing failure during the long term time period. Multiple environmental conditions lead to the sensing failure. For example, corrosion of electrical components of the pressure sensor lead to the sensing failures. Ions in the operational environment are responsible for the corrosion. As described herein above, hydrophobicity of the liquid protects against the corrosion. In addition, biofouling negatively impacts the sensitivity and offset drift of the pressure sensor. The shape and size of the package's outer membrane protects against the biofouling's impact. The shape and size of the outer membrane form a surface configuration of the package that can be designed to protect against biofouling, among other things.

As illustrated, the pressure sensor 710 is encapsulated with a volume 720 of hydrophobic liquid 740. An outer membrane 730 is formed by depositing silicone, parylene-C, parylene-D, a polyimide, and/or a thin metal around an outer surface of the volume 720. The outer membrane 730 has a concave curvature with respect to outside its enclosed volume. The concavity is selected by design and effectuated through a manufacturing method. By design, the manufacturing environment and the operational environment can have different temperatures. If the manufacturing temperature is smaller than the operational temperature, the hydrophobic liquid 740 is expected to expand in the operational environment. In this case, the surface configuration can be designed to be concave. The concavity allows the outer membrane 730 to bend rather than expand in operation. Conversely, if the manufacturing temperature is higher than the operational temperature, the surface configuration can be designed and manufactured to be convex.

Various manufacturing techniques are available to effectuate a desired curvature of the surface configuration. As illustrated, posts are added to the package. For example, a post 742, a post 744, a post 746, and a post 748 are attached to the pressure sensor 710. A post represents an arm made out of a rigid biocompatible material. One end of the post is disposed on, for instance, an outer surface of the pressure sensor 710. In an example, the post is attached to the outer surface via a biocompatible epoxy. The other end extends outwardly from the outer surface of the pressure sensor 710.

Optionally, one or more holes 750 exist between the two ends within the pole. The hole(s) 750, when present within the pole, allows the flow of the hydrophobic liquid through the pole.

The surface configuration, whether concave or convex, is created based on the kinematic viscosity of the hydrophobic liquid and the tension surface of the post. For example, a concave meniscus occurs between two posts when the cohesion within the hydrophobic liquid is weaker than the adhesion to the two posts. Conversely, a convex meniscus occurs when the cohesion within the hydrophobic liquid is stronger than the adhesion to the two posts. Once the desired meniscus is achieved, silicone, parylene-C, parylene-D, a polyimide, and/or a thin metal is deposited to surround the free surface of the hydrophobic liquid and the exposed end of the pole. In the illustration of FIG. 7, the surface configuration includes four concave curvatures. Each of the concave curvatures occur between two adjacent posts.

Other manufacturing techniques can also be used. Such techniques need not use posts. For example, a solid material with melting temperature in between deposition temperature and temperature of operation is added to the volume 720 of hydrophobic liquid 720. Parylene-C or and/or parylene-D is deposited on a surface of the volume 720 of hydrophobic liquid 740 and the solid. In an example, the solid includes at least octadecane and has a melting temperature of about 29° C. (84.2° F.). In comparison, the deposition temperature of the parylene-C or and/or parylene-D is about 21° C. (69.8° F.). The operating temperature (e.g., the body temperature) is about and 37° C. (98.6 F). Hence, octadecane (or another solid with similar melting properties) is deposited on the outer surface of the pressure sensor 710 during the manufacturing of the package. The volume 720 of hydrophobic liquid 740 is then added and encapsulated using the outer membrane 730. In operation, the operational temperature leads to the melting of the octadecane. The hydrophobic liquid moves to occupy the freed volume, resulting in a curvature of the outer membrane 730. In a particular illustration of this manufacturing technique, octadecane as a solid can be molded or shaped by any method to then possibly sit in the volume 720 pool of hydrophobic liquid 740. The outer membrane 730 is subsequently coated. In operation (e.g., the package assembly 700 implanted in a human body), the temperature of the package assembly 700 rises to the temperature of the operational environment (e.g., to the human body's temperature). The temperature rise results in the solid octadecane melting and mixing with the hydrophobic liquid 740. The result is a liquid volume encapsulated in situ that still has a designed surface configuration. An example of octadecane-based shaping is further illustrated in FIGS. 17A, 17B, 17C, and 17D.

Other surface configurations can also be used to protect against biofouling. For example, corrugations, such as wrinkles or folds, are induced in the outer membrane. The corrugations allow the expansion of the hydrophobic liquid when the operational temperature is larger than the manufacturing temperature. Different manufacturing techniques are also available to induce the corrugations. For example, octadecane can also be used. In another example, the package is manufactured in a mold. The surface of the mold include the corrugations. In yet another example, the outer membrane 730 is annealed past a yield strength of the material that the outer membrane 730 is made of, followed by and cooling of the annealed membrane to lower temperatures.

Figure 8:
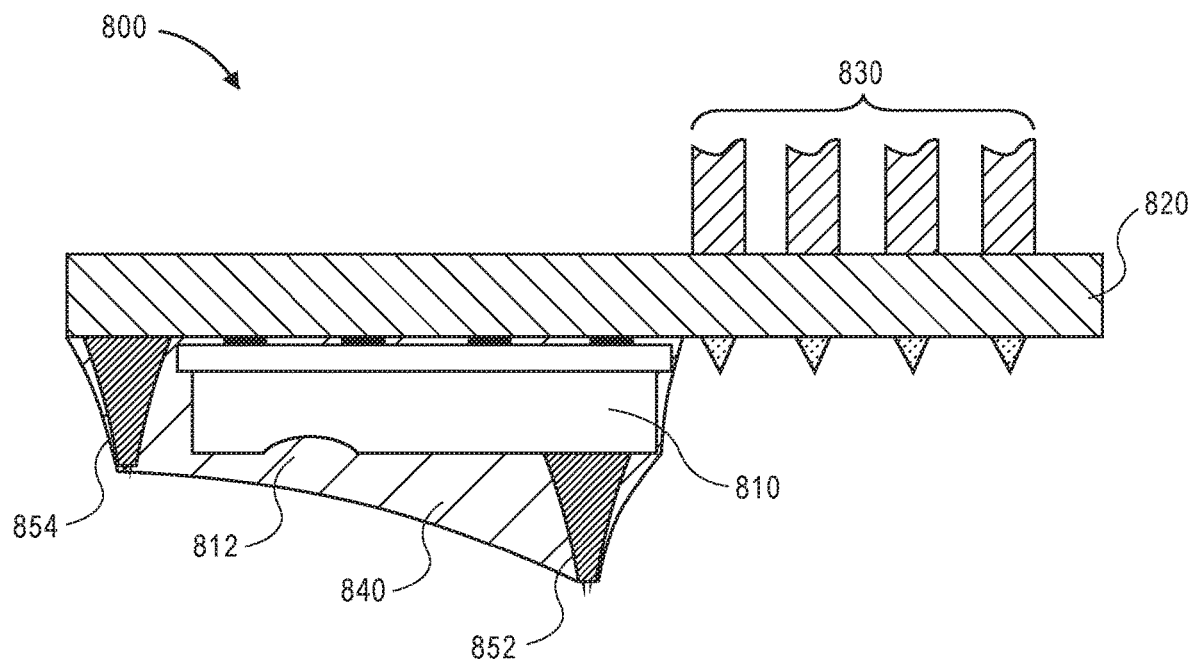
FIG. 8 illustrates an example volume of hydrophobic liquid around a pressure sensor of an implantable medical device, in accordance with an embodiment.

FIG. 8 illustrates an example package assembly 800 of a pressure sensor 810 of a medical device, where the package includes a concave curvature for a portion of an outer membrane. In this example, a Freescale® MPL115A1 miniature serial peripheral interface (SPI) digital barometer available from Freescale Semiconductor, Inc. of Austin, Texas is protected with a liquid encapsulation.

The package assembly 800 illustrates a design choice to keep electronics protected from corrosion from water vapor or other contaminants. To do so, one approach is to change the chemical environment that the pressure sensor 810 is exposed to while in operation, rather than relying on a barrier. This is achieved by housing the electronics in a hydrophobic liquid, such as silicone oil, to reduce the saturation limit of water vapor in the sensor's environment. In silicone oil the saturation limit of water vapor is around 350 parts per million (ppm) at 37° C. (98.6° F.). Silicone oil is superior to silicone, because even though both repel liquid water, only the oil repels water vapor, while water vapor is drawn towards inevitable defects in the silicone. One of the purposes of the parylene is to encapsulate the oil so it remains where it needs to be. The membrane may be composed of multiple materials, as long the encapsulating film is flexible enough, can block corrosive chemical and/or biological agents, is biocompatible, and is mechanically reliable.

As illustrated, the pressure sensor 810 of this barometer is disposed on (e.g., soldered onto) an electromechanical substrate 820, such as a printed circuit board (PCB). Generally, the electromechanical substrate 820 may but need not be biocompatible. In an example, the electromechanical substrate 820 includes one or more of a wireless communication circuit element, a power management circuit element, a signal processing circuit element, a power harvesting circuit element, or a set of conductive wires. Ends of wires 830 are also soldered onto the electromechanical substrate 820. The wires 830 electrically couple the pressure sensor 810 with non-implantable components of the medical device and/or of the medical system.

The pressure sensor 810 is dipped in an incompressible 30,000 cSt ($3\times10^{-2}$ $m^2/s$) silicone oil 840 and, as further illustrated in the next figure, encapsulated by chemical vapor deposited (CVD) parylene. This results in an oil packaging that is free of bubbles and hermetically sealed by parylene. The silicone oil 840 surrounds a pressure port 812 of the pressure sensor 810. By design, the shape of the silicone oil 840 is concave such that, even if the environmental temperature varies and causes oil volume changes, the parylene will bend rather than expand in tension.

Prior to the oil dipping, degassing is performed. For instance, a low-kinematic viscosity diluent, such as a low-kinematic viscosity hexane, is used for the degassing. The hexane (or, as applicable, other user diluent) fills the hydrophilic void inside the pressure port 812, then gets diffused and replaced by oil, greatly accelerating the degassing process. Also, during degassing a temporary guard is placed on the electromechanical substrate 820 such that oil would not splatter on the electromechanical substrate 820 near the wires when bubbles pop. After degassing, the sensor is held face down in a parylene deposition chamber. The high-kinematic viscosity silicone oil does not form droplets nor fall off for hours.

To achieve the concave curvature, a silicone post 852 is epoxied to a free surface of the pressure sensor 810. Another silicone post 854 is also epoxied to a free surface of the electromechanical substrate 820, opposite to the silicone post 852 from the pressure sensor 810. In addition, the silicone oil 840 has a high kinematic viscosity such that the silicone oil 840 could be hung upside-down and not fall for a sufficiently long time so that parylene can be coated on the free surface of the silicone oil 840. The orientation in which the pressure sensor 810 is held, the locations and sizes of the silicone post 852 and silicone post 854, and the high kinematic viscosity of the silicone oil 840 result in the concave curvature.

Although FIG. 8 illustrates two posts, a different number of posts can also be used. In addition, the two posts need not be of the same size or material. Likewise, the posts (whether two or more) could be distributed across other locations. For example, the two posts can be attached to pressure sensor 810 or to the electromechanical substrate 820.

Figure 9:
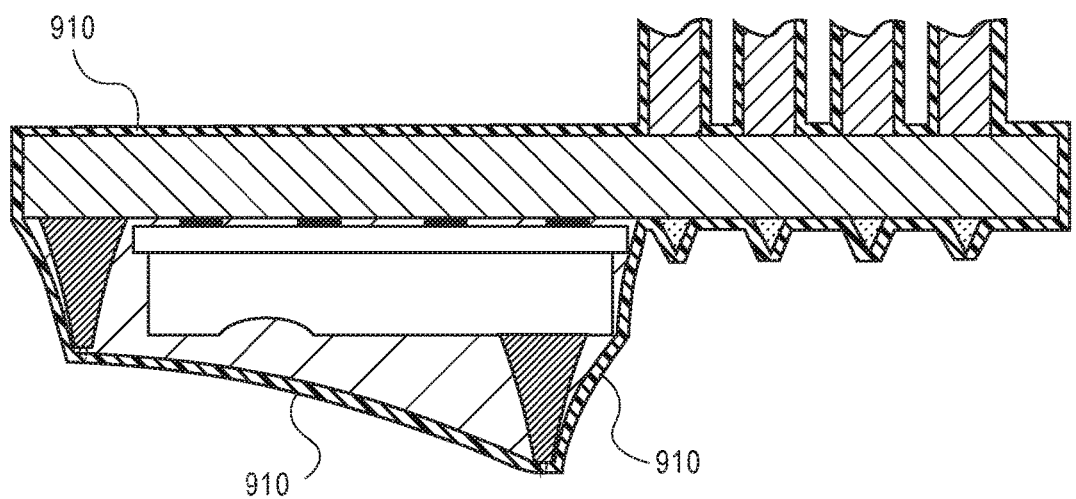
FIG. 9 illustrates an example outer membrane formed around a volume of hydrophobic liquid, in accordance with an embodiment.

FIG. 9 illustrates an outer membrane 910 of the package described in connection with FIG. 8. In particular, thick parylene is used as an isolation barrier from biomolecules to avoid direct biofouling of the pressure sensor (e.g., the pressure sensor 810). Biofouling on outer parylene is minimal and would not affect the pressure transmission due to larger surface area.

As illustrated, silicone, parylene-C, and/or parylene-D is coated via CVD. The coating is applied to a free surface of the silicone oil (e.g., the silicone oil 840) and, optionally, to free surfaces of other implantable components of the medical device. These other implantable components include posts (e.g., the post 852 and the post 854), an electromechanical substrate (e.g., the electromechanical substrate 820), and ends of wires (e.g., the wires 830).

Figure 10:
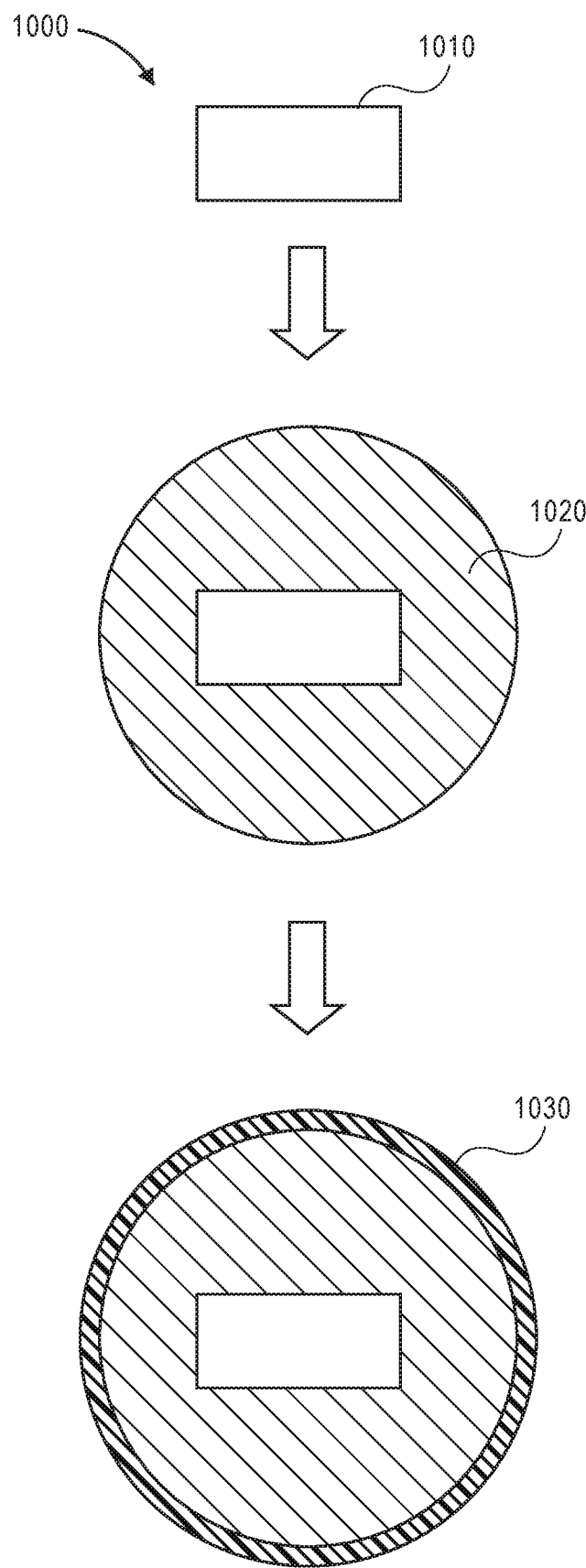
FIG. 10 illustrates example steps for packaging an implantable medical device, in accordance with an embodiment.

FIG. 10 illustrates a manufacturing process 1000 to package an implantable component 1010 of a medical device, where the packaging uses liquid encapsulation. The implantable component 1010 includes one or more of sensors, actuators, electrical components, electronic components, mechanical components, or substrates carrying such components. In an example, the implantable component 1010 is degassed. Upon degassing, a hydrophobic liquid is deposited on a free surface of the implantable component 1010 to form a volume 1020. As illustrated, the volume 1020 contains the entire implantable component 1010. However, the hydrophobic liquid can alternatively be deposited on only a portion of the free surface such that the volume 1020 partially contains the implantable component 1010. An outer membrane 1030 is formed around the outer perimeter of the volume 1020. For example, polymer material is deposited through CVD on the outer perimeter to form a non-porous and flexible outer membrane 1030.

This manufacturing technique may be applied repeatedly to create multiple liquid encapsulation layers. In addition, the manufacturing technique may include inducing a particular surface configurations of the outer membrane 1030.

Figure 11:
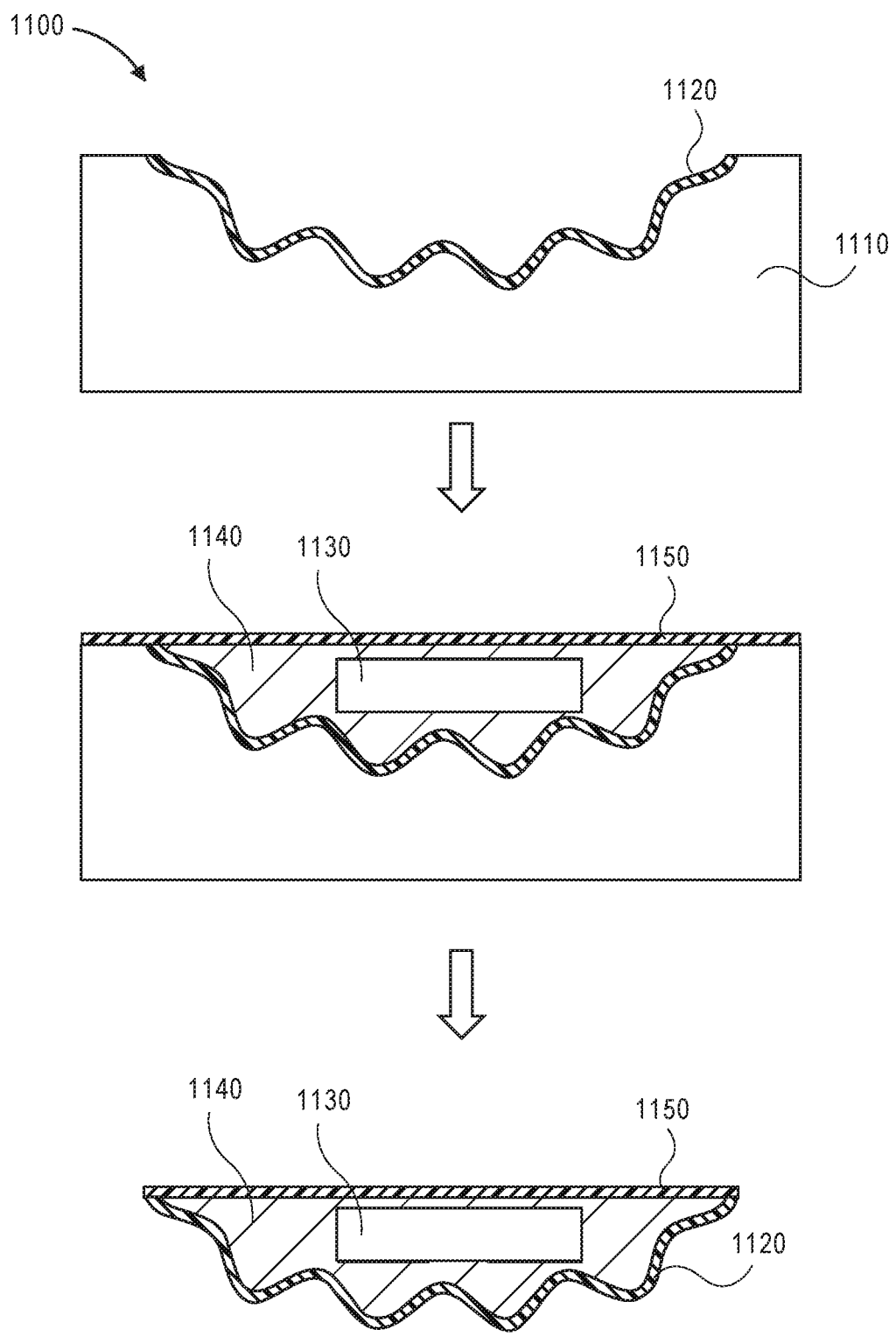
FIG. 11 illustrates other example steps for packaging an implantable medical device, in accordance with an embodiment.

FIG. 11 illustrates an example manufacturing process 1100 for liquid encapsulation. The illustrated process uses a cast of mold 1110. The mold 1110 is degassed. A surface of the mold 1110 is coated with a polymer material to create a membrane 1120. The surface can include corrugations such that the corrugations are induced in the membrane 1120.

An implantable component 1130 of a medical device is degassed and placed in the mold 1110. A hydrophobic liquid is poured into the mold 1110 to create a volume 1140 around the implantable component 1130. A portion of the volume's perimeter is bound by the membrane 1120. The remaining portion of the perimeter is free. A same or a different polymer material is deposited on the remaining portion to form a second membrane 1150 such that the membrane 1120 and the membrane 1150 seal the volume 1140 and the implantable component 1130.

Thereafter, the package formed by the membrane 1120, the membrane 1150, and the volume 1140 of hydrophobic liquid is removed from the mold 1110. The package contains the implantable component 1130. The membrane 1120 and the membrane 1150 represent an outer membrane of the package.

This manufacturing technique may be applied repeatedly to create multiple liquid encapsulation layers or may be used to encapsulate only a portion of the implantable component 1130. In addition, the manufacturing technique may include inducing other particular surface configurations of the outer membrane.

Figure 12:
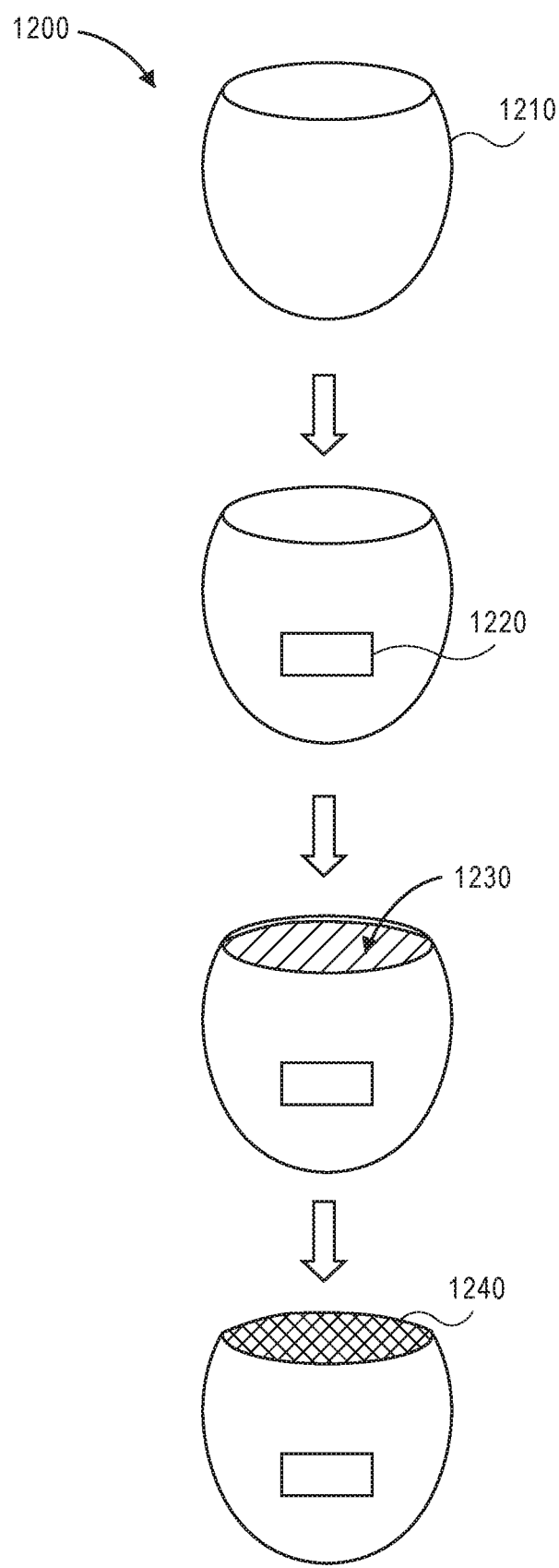
FIG. 12 illustrates yet other example steps for packaging an implantable medical device, in accordance with an embodiment.

FIG. 12 illustrates an example manufacturing process 1200 for liquid encapsulation. The illustrated process uses a mold polymer bag 1210. The polymer bag 1210 is formed out of a polymer material through CVD and includes an opening. The polymer bag 1210 is degassed. An implantable component 1220 of a medical device is degassed and placed inside the polymer bag 1210 through the opening. A hydrophobic liquid is also poured into the polymer bag 1210 through the opening to create a volume 1230 around the implantable component 1220. The volume 1230 can correspond to (e.g., be substantially equal to) or be smaller than the inner volume of the polymer bag 1210. A portion of the volume's perimeter is bound by the polymer bag 1210. The remaining portion of the perimeter is free. A same or a different polymer material is deposited on the hydrophobic liquid through the opening (e.g., on a free surface of the volume 1230) to create a membrane 1240 and seal the volume 1230 and the implantable component 1220 (e.g. to close the opening). The package is formed by the polymer bag 1210, the membrane 1240, and the volume 1230 of hydrophobic liquid. The polymer bag 1210 and the membrane 1240 represent an outer membrane of the package.

This manufacturing technique may be applied repeatedly to create multiple liquid encapsulation layers or may be used to encapsulate only a portion of the implantable component 1220. In addition, the manufacturing technique may include inducing particular surface configurations of the outer membrane.

FIG. 13 illustrates an example manufacturing method 1300 to package an implantable component of a medical device, where the packaging uses liquid encapsulation. The implantable component includes one or more of commercial off-the-shelf (COTS) sensors, actuators, electrical components, electronic components, mechanical components, or substrates carrying such components. In the interest of clarity of explanation a sensor is described in connection with the manufacturing method as an example of the implantable component. In addition, the described steps of the manufacturing method can be performed in any order.

A step 1302 of the manufacturing method includes forming a volume of hydrophobic liquid around at least a portion of the sensor. The portion includes an operational component of the sensor that should be protected against conditions of an operational environment for the sensor to properly function. For instance, in the case of a pressure sensor, the portion includes a pressure port. The volume can also be extended to cover or surround the entire sensor rather than being limited to the portion. Different manufacturing techniques are available to form the volume. As described in FIGS. 10, 11, and 12, these techniques include any of depositing the hydrophobic liquid directly on at least the portion of the sensor, placing the sensor in a volume and pouring the hydrophobic liquid in the volume, and/or placing the sensor in a volume that already contains the hydrophobic liquid. The step 1302 can also include degassing at least the portion of the sensor and/or inducing a particular curvature design of a free surface of the volume of hydrophobic liquid. Inducing the curvature design may be performed by using posts, and/or octadecane material.

A step 1304 of the manufacturing method includes forming a flexible outer membrane. This membrane is formed on a free surface of the volume. In the case where the volume surrounds the entire sensor, the membrane can extend around the entire volume to also surround the entire sensor. In the case where the volume surround only the portion of the sensor, the membrane is formed on the free surface of the volume, where this free surface is not in direct contact with the portion of the sensor. The outer membrane can also be extended around the remaining portion of the sensor. For instance, the outer membrane can form a protective layer in direct contact with the remaining portion of the sensor. Different manufacturing techniques are available to form the flexible outer membrane. As described in FIGS. 10, 11, and 12, these techniques include any of depositing polymer material on a free surface of the volume of hydrophobic liquid through CVD, coating and sealing via a mold, and/or sealing a polymer bag. The step 1304 can also include degassing the flexible membrane (e.g., when a mold or a polymer bag is used), and/or inducing a particular curvature design. Inducing the curvature design may be performed by using posts, octadecane material, mold corrugations, and/or annealing and cooling the flexible outer membrane.

The above steps of the manufacturing method can be repeated to create a multiple layer liquid encapsulation of the sensor. Similarly, the steps can be repeated across a plurality of sensors (or other implantable components) contained within a medical device. The manufacturing method can also include additional steps. In an example, a rigid assemblage is formed and added inside or outside the package for additional protection.

FIG. 14 illustrates an example of a manufacturing method 1400 to package the implantable component. The steps described within this example can be used as sub-steps of the example manufacturing method of FIG. 13.

A step 1402 of the manufacturing method 1400 includes degassing at least the portion of the sensor. For instance, the sensor is held in a particular orientation (e.g., upside down) and a low-kinematic viscosity gas, such as hexane, is used for the degassing.

A step 1404 of the manufacturing method 1400 includes placing at least the degassed portion of the sensor in a solution of hydrophobic liquid. For instance, once degassing is complete, the sensor is entirely or partially (e.g., the portion of the sensor) dipped in the solution. Alternatively, the hydrophobic liquid is poured directly on the sensor (or the portion of the sensor). Once the sensor is fully or partially is in place, the hydrophobic liquid forms a volume that fully or partially surround the sensor.

A step 1406 of the manufacturing method 1400 includes depositing a polymer material on a surface of the volume of the hydrophobic liquid. For instance, the polymer material includes one or more of silicone, parylene-C, or parylene-D and is deposited through CVD.

A step 1408 of the manufacturing method 1400 incudes inducing a particular curvature design. In an example, the curvature design is induced by attaching ends of posts to locations on the sensor (and/or a supporting electromechanical substrate) and by using particular hydrophobic liquid and material for the posts to achieve a desired meniscus. In another example, octadecane material is deposited on at least the portion of the sensor prior to the addition of the hydrophobic liquid such that the hydrophobic liquid surrounds the octadecane material. In yet another example, the octadecane material is additionally or alternatively deposited on a free surface of the hydrophobic liquid prior to the deposition of the polymer material such that this polymer material is deposited on the octadecane material instead of the hydrophobic liquid. The curvature design can be induced following any of the step 1402 and prior to the step 1404, the step 1404 and prior to the step 1406, and/or the step 1406.

Figure 15:
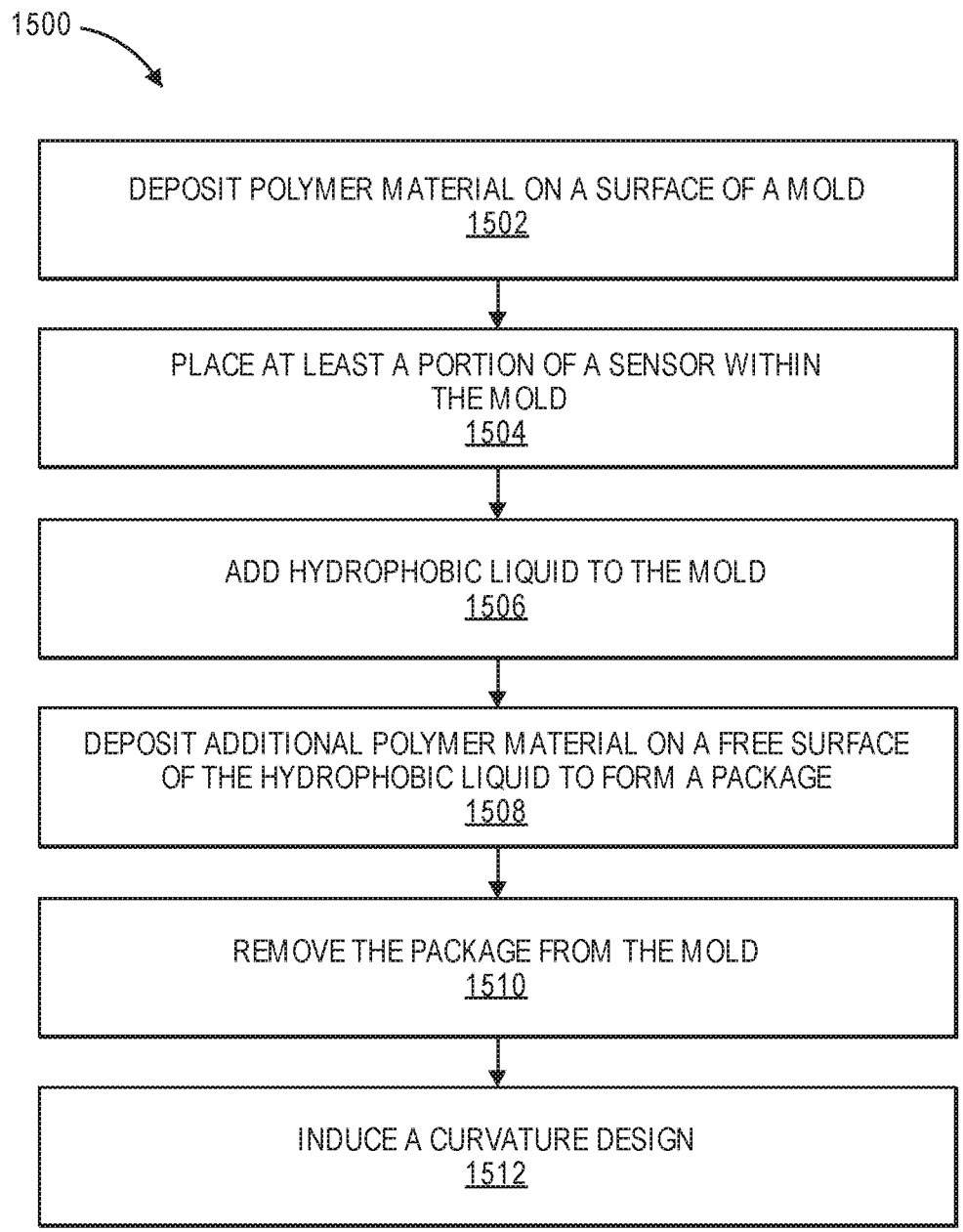
FIG. 15 is a flowchart with another example of a more detailed method for manufacturing an implantable medical device packaged for protection against conditions of an operation environment, in accordance with an embodiment.

FIG. 15 illustrates an example of a manufacturing method 1500 to package the implantable component. The steps described within this example can be used as sub-steps of the example manufacturing method of FIG. 13.

A step 1502 of the manufacturing method 1500 includes depositing a polymer material on a surface of a mold. For instance, the polymer material includes one or more of silicone, parylene-C, or parylene-D. The mold includes a cavity. A surface of the cavity is coated with the polymer material to form a membrane.

A step 1504 of the manufacturing method 1500 includes placing at least the portion of the sensor within the mold. For instance, the sensor is fully or partially (e.g., the portion of the sensor) inserted in the cavity of the mold.

A step 1506 of the manufacturing method 1500 includes adding hydrophobic liquid to the mold. For instance, the hydrophobic liquid is poured into the mold and surrounds entirely or partially the placed sensor.

A step 1508 of the manufacturing method 1500 includes depositing additional polymer material on a free surface of the hydrophobic liquid. For instance, the free surface is at an outer perimeter of the volume formed by the hydrophobic liquid. The outer perimeter is located away from the existing membrane formed in step 1502 and located toward the opening of the cavity of the mold. The polymer material need not but can be the same as the polymer material used in step 1502. The deposition results in a second membrane that, collectively with the existing membrane, seal the hydrophobic liquid and the sensor (fully or partially dependent on the sensor placement in step 1504). The two membranes and the hydrophobic liquid form a liquid encapsulation package.

A step 1510 of the manufacturing method 1500 includes removing the package from the mold. For example, the package is ejected from the cavity through the form of the mold. Once removed, different finishing can be applied to the package, such as to remove excess deposited material.

A step 1512 of the manufacturing method 1500 incudes inducing a particular curvature design. In an example, the curvature design is induced by corrugations. For instance, the surface of the cavity where the polymer is deposited also includes corrugations. These corrugations are transferred to the membrane created in step 1502 through the deposition of the polymer material on the surface of the cavity.

Figure 16:
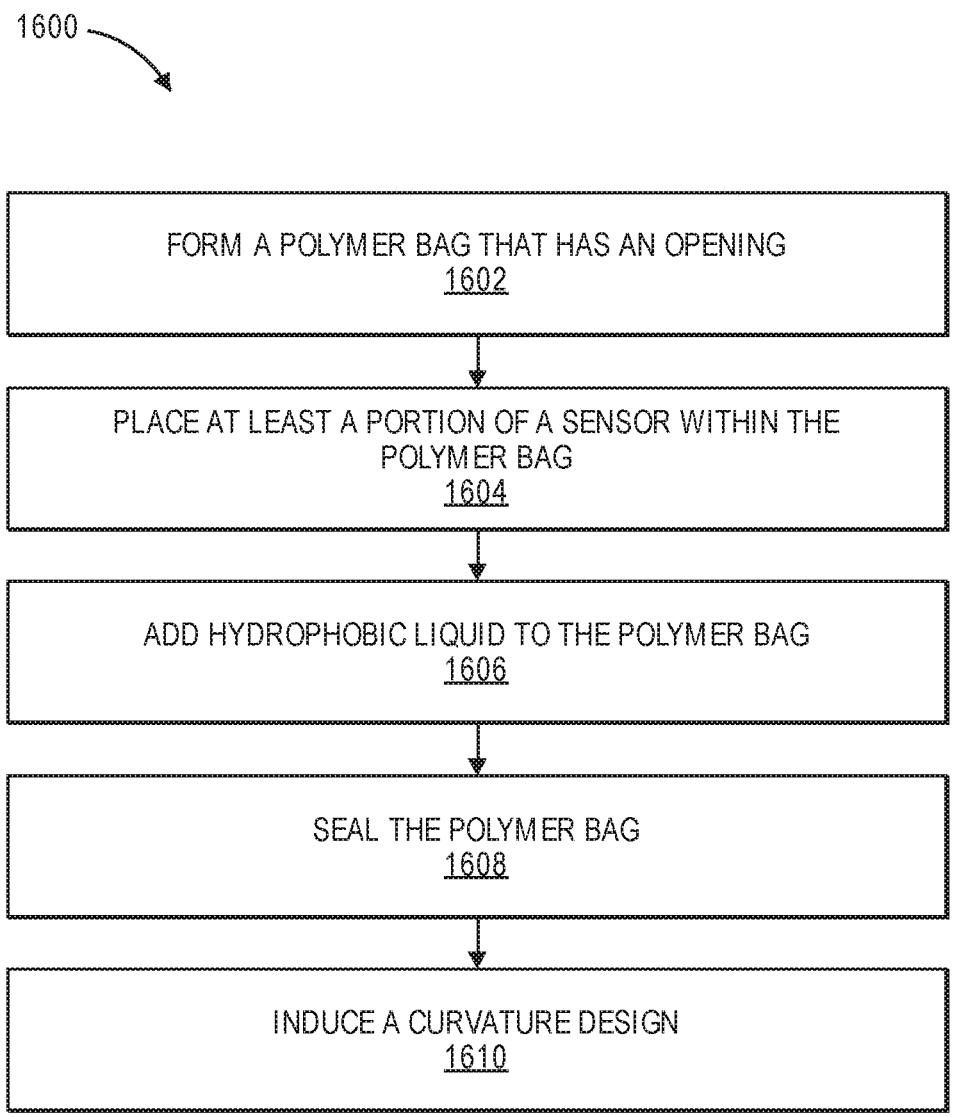
FIG. 16 is a flowchart with yet another example of a more detailed method for manufacturing an implantable medical device packaged for protection against conditions of an operation environment, in accordance with an embodiment.

FIG. 16 illustrates an example of a manufacturing method 1600 to package the implantable component. The steps described within this example can be used as sub-steps of the example manufacturing method of FIG. 13.

A step 1602 of the manufacturing method 1600 includes forming a polymer bag that has an opening. For instance, a polymer material is used to form the bag through a CVD on a bag-shaped like mold. The polymer material includes one or more of silicone, parylene-C, or parylene-D.

A step 1604 of the manufacturing method 1600 includes placing at least the portion of the sensor within the polymer bag. For instance, the sensor is fully or partially (e.g., the portion of the sensor) inserted in the polymer bag through the opening.

A step 1606 of the manufacturing method 1600 includes adding hydrophobic liquid to the polymer bag. For instance, the hydrophobic liquid is poured into the polymer bag through the opening and surrounds entirely or partially the placed sensor.

A step 1608 of the manufacturing method 1600 includes sealing the polymer bag. For instance, the opening is sealed by depositing a polymer material on a free surface of the hydrophobic liquid through the opening. The polymer material need not but can be the same as the polymer material used in step 1602.

A step 1610 of the manufacturing method 1600 incudes inducing a particular curvature design. In an example, the curvature design is induced by corrugations. For instance, the surface of the polymer bag is manufactured to include corrugations. These corrugations are created by annealing the polymer bag past a yield strength of the underlying polymer material and cooling the annealed polymer bag to lower temperatures. The annealing and cooling can be performed prior to or after the placement of the portion of the sensor, as in step 1604, addition of the hydrophobic liquid, as in step 1606, and/or the sealing of the polymer bag, as in step 1608.

FIGS. 17A, 17,B, 17C, and 17D illustrate an example of octadecane-based shaping of a surface curvature. FIG. 17A illustrates step 1710 of the shaping, where a pressure sensor is placed in an open face enclosure and is covered with oil. A bowl-shape octadecane solid piece (or some other desired curvature) is placed on top of the pressure sensor. FIG. 17B illustrates another step 1720 of the shaping, where parylene-C or parylene-D is deposited to cover at least the octadecane solid piece. The deposition occurs at room temperature of about 21° C. (69.8° F.). FIG. 17C illustrates another step 1730 of the shaping, where after the pressure sensor is packaged and implanted in a human body, the octadecane solid piece melts at the body temperature of about 37° C. (98.6° F.). The liquid octadecane is a hydrophobic liquid. This results in a bowl-like shape of the parylene outer membrane. FIG. 17D illustrates another step 1740 of the shaping, where the oil and liquid octadecane expand at higher elevated temperatures, but the parylene outer membrane is not streched. Rather, the parylene outer membrane is bent up to a higher temperature limit than could be possible without the use of octadecane.

For a numerical example, suppose that a pressure sensor package has an area of 3 mm×3 mm (0.12 inches×0.12 inches) area and 1 mm (0.39 inches) tall. The pressure sensor cavity is a 1 mm³ volume (6.1×10⁻⁵ cubic inch), centered. Thus if the pressure sensor membrane is submerged, there is roughly 8 mm³ (4.9×10⁻⁴ cubic inch) of silicone oil. Suppose that there is a paraboloid bowl, of base radius R=1 mm (0.39 inches), height h=0.2 mm (0.078 inches).

$$y = \frac{h}{R^2} r^2.$$

Thus the volume of me octadecane bowl is a simple integration resulting in $$V = \frac{\pi h R^2}{2}.$$

The slack volume is twice the volume the bowl could carry. $V_{slack} = \pi h R^2$. The coefficient of thermal expansion for silicone oil and octadecane is roughly 0.1%/° C.

The volume expansion when octadecane melts is 20%. Thus the slack volume should reduce to roughly 80% of the original value. Plugging in the values, $V'_{slack} \approx 0.8 * \pi h R^2 \approx 0.5$ mm³ (3×10⁻⁵ cubic inch). The volume of oil plus volume of octadecane (liquid) is 8.3 mm³ (5×10⁻⁴ cubic inch).

$$\frac{0.5 \text{ mm}^3}{8.25 \text{ mm}^3} \approx 0.06.$$

Thus the octadecane provides a slack of 6% of the total liquid volume. This equates to roughly 60° C. (108° F.) worth of temperature expansion without stretching the parylene, only bending.

In a lab experiment, an MPL115A1 miniature SPI digital barometer was packaged in a manner similar to the packaging described in connection with FIGS. 8 and 9. A silicone oil of about 30,000 cSt (3×10⁻² m²/s) and a parylene-D outer membrane of about 26.64 μm (0.001 in) thickness are used for the packaging. The sensor outputs 10-bit pressure and temperature data and the calibration data was captured after heating the sensor dry in a 77° C. (170.6° F.) oven overnight, at 21° C. (69.8° F.), 37° C. (98.6° F), and 45° C. (113° F.). Calibration considered the output pressure using the calibration constants from the sensor itself, adjusted up to a linear relationship with raw pressure and temperature output and a constant offset. The pressure sensitivity of the packaged sensor was found to be substantially the same as the pressure sensitivity of an unmodified sensor. The packaged sensor was also found to have a quick step response, substantially similar to the step response of the unmodified sensor.

In addition, various pressure sensors were investigated for accelerated soaking tests. A control sensor was uncoated and failed as expected after one day in 67° C. (152.6° F.) saline. Other sensors were coated with parylene-C (PA-C) or parylene-D (PA-D) without oil. The remaining sensors were packaged with 30,000 cSt ($3\times10^{-2}$ m²/s) silicone oil and encapsulated with parylene-C or parylene-D. All of the devices were thermally stressed in air overnight at the temperature at which they were to be soaked to determine isolate sensitivity and offset drift due to elevated temperature versus soaking in saline. The results are summarized in Table 1.

In the lab experiment, another pressure sensor was not modified nor given a thermal regiment before soaking in 5,000 cSt ($5\times10^{-3}$ m²/s) silicone oil at 97° C. (206.6° F.), since the water saturation limit increases at elevated temperatures. At 97° C. (202.6° F.), the saturation limit of water is around 1,000-1,500 ppm. After the first week a small offset of the sensor was induced, presumably due to thermal treatment. However, the offset and the sensitivity did not change the following weeks. This result confirms that silicone oil is not meaningfully harmful to the pressure sensor.

TABLE 1

| Package | Unit Time/Temp. |  | Pre-Soak | 1 | 2 | 3 | 4 | 5 | 6 | 7 |
|---|---|---|---|---|---|---|---|---|---|---|
| Oil + 20.6 μm PA-C | Week/87° C. | Sensitivity | 1.050 | 1.026 | 1.073 | 1.023 | 0.996 | 0.248 | | |
| | | Offset. (kPa) | 0.423 | −19.4* | −21.8 | −21.3 | −21.4 | 10.73 | | |
| No Package | Day/67° C. | Sensitivity | 1.015 | | | | Failed | | | |
| | | Offset (kPa) | 1.753 | | | | | | | |
| Oil + 26.64 μm PA-D | Week/77° C. | Sensitivity | 1.001 | 1.000 | 0.993 | 1.001 | 0.999 | 0.994 | 0.997 | 0.973 |
| | | Offset (kPa) | −0.512 | −0.119 | −0.048 | 0.300 | −0.155 | −0.02 | 0.286 | 1.116 |
| Oil + 24.92 μm PA-D | Week/77° C. | Sensitivity | 0.996 | 1.000 | 1.001 | 0.999 | Failed due to wire corrosion | | | |
| | | Offset (kPa) | −0.854 | −0.574 | −0.204 | 0.061 | | | | |
| ~13.17 μm PA-D 1 | Week/77° C. | Sensitivity | 0.979 | 0.987 | 0.983 | 0.980 | 0.995 | | Failed | |
| | | Offset (kPa) | 48.37 | 52.47 | 53.12 | 48.52 | 55.50 | | | |
| ~13.17 μm PA-D 2 | Week/77° C. | Sensitivity | 0.971 | 0.974 | 0.978 | 0.955 | 0.972 | 0.969 | 0.986 | 0.976 |
| | | Offset (kPa) | 49.96 | 53.68 | 54.51 | 51.04 | 54.67 | 55.60 | 56.13 | 55.82 |
| 5000 cSt Oil Bath | Week/97° C. | Sensitivity | 0.998 | 0.997 | 0.998 | 0.998 | 0.996 | 0.997 | | |
| | | Offset (kPa) | −0.222 | −0.468 | −0.468 | −.446 | −0.410 | −.443 | | |
| (no saline) | | | 8 | 9 | 10 | 11 | 12 | 13 | 14 | 15 |
| Oil + 26.64 μm PA-D | Week/77° C. | Sensitivity | | | | Failed | | | | |
| | | Offset (kPa) | | | | | | | | |
| ~13.17 μm PA-D 2 | Week/77° C. | Sensitivity | 0.990 | 1.000 | 0.978 | 0.996 | 0.986 | 0.983 | 0.987 | Failed |
| | | Offset (kPa) | 55.51 | 57.6 | 56.43 | 56.44 | 55.71 | 53.47 | 36.00 | |

It was found that roughly every 10° C. (18° F.) doubles the acceleration factor of parylene due to the Arrhenius relationship with exponent of around −0.61 eV ($-9.6\times10^{-20}$ J). It was also found that thicker layers of PA-C would not survive higher temperatures in attempting to achieve faster acceleration factors so devices were instead packaged with PA-D due to its higher glass transition temperature so saline tests could more quickly and efficiently determine lifetime at 37° C. (98.6° F.).

The longest lasting device while maintaining adequate sensitivity and offset with PA-D is "Oil+26.64 μm PA-D" which lasted for six weeks at 77° C. (170.6° F.), equivalent to twenty-one months at 37° C. (98.6° F.). At this point a bubble was observed, possibly due to delamination of the parylene with the PCB substrate, leading to a void volume during vacuum, which could be filled by air permeating through the membrane. A leak was not observed.

The device "Oil+24.92 μm PA-D" showed instability in getting a signal in the third week when it was noticed that the wires used to investigate the device had fallen under the saline leading to corrosion. These wires may not be present in a final device so they were not submerged, yet by the fourth week, a stable signal was not obtainable. So, it was deemed that the electronics failed for this reason. However the device "~13.17 μm PA-D 1" may have suffered delamination by the fifth week at the membrane, consistent with the observation of sensitivity climbing to about "1" and then the signal becoming unstable and unobtainable the next week even though the wires were never submerged.

It was also found that degassing is advantageous and allows to properly soak devices without oil and prevent bubble formation in the cavity that prevents saline from contacting the membrane.

A model of pressure transduction efficiency of a parylene-on-oil package "η" is derived for a pressure sensor assuming incompressible liquid. Through mathematical derivation, "η" is found as $$"\eta = \frac{c_2}{c_1 + c_2},"$$

where "$c_1$" is the volume-pressure compliance of the membrane of the pressure sensor and "$c_2$" is the volume-pressure compliance of the outer flexible membrane. Generally, $$"c \propto \frac{a^6}{t^3},"$$

where "a" is a respective radius (for circular membranes, and another dimension for other geometric shape), and "t" is the membrane's thickness. Accordingly, increasing the effective outer radius has a large impact on "$c_2$", making it quite easy to achieve large enough volume-pressure compliance (e.g., "η≈1") on the outer membrane such that loss of pressure transduction is negligible, and tissue accumulation on the large outer membrane will cause negligible drift in the value of "η" as well, despite a possibly large fractional change on "$c_2$", as long as "$c_2$" still remains large compared to "$c_1$."

The sensitivity to biofouling can also be estimated. Generally, the larger exterior membrane means that, for the same thickness of biofouling, the effect on the sensitivity is less than if the pressure sensor was directly covered with parylene. In other words, the sensitivity drift is predicted to be nil with the parylene-on-oil packaging. There can be situations where it is hard to discern whether a change in the pressure reading is due to sensitivity drift or actual change in pressure. In such situations, it becomes important to understand that the sensitivity drift can appear to look like large offset drift depending on the typical value intended to be measured relative to the constant pressure inside the pressure sensor chamber.

An upper bound on tolerable sensitivity drift can be estimated. Consider an example of using the pressure sensor to monitor blood pressure. The average pressure of blood is roughly 100 mmHg (1.93 psi) compared to atmosphere. Generally, such blood pressure monitoring may need a 1 mmHg (0.0193 psi) resolution. Thus, even ignoring offset drift, the sensitivity drift must be at most 1%. For this reason, multiple recalibrations and/or schemes to eliminate biofouling may not achieve this tight tolerance. Instead, the outer membrane which mechanically eliminates sensitivity drift can be a robust, effective solution.

In a simulation, a pressure sensor was packaged with a 10 µm ($3.9 \times 10^{-4}$ inches) PA-D parylene-on-oil liquid encapsulation resulting in a square membrane 3mm on a side, which is the footprint of the plastic package. The parylene-on-oil packaged pressure sensor exhibits effectively no sensitivity drop or sensitivity drift. In comparison, a parylene-only packaged pressure sensor exhibits 58% sensitivity when clean, and drops to 47% at 100 µm ($3.9 \times 10^{-3}$ inches) of biofouling (i.e., a sensitivity drift of 18%). While biofouling is found to cause pressure due to contractile forces of the fibrous capsule, that would not contribute to sensitivity drift in the parylene-on-oil scheme.

Exploiting parylene deposition via CVD directly on oil, a parylene-on-oil packaging of implantable pressure sensors can lengthen the lifetime of these sensors. Silicone oil suppresses water content in the sensor's environment, and parylene encapsulates the oil without any bubbles. Because of increased surface area of the outer membrane, the protective benefits of thick parylene can be used without sacrificing sensitivity. The increased surface area may also reduce the sensitivity drift from biofouling.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain. "About" includes within a tolerance of ±0.01%, ±0.1%, ±1%, ±2%, ±3%, ±4%, ±5%, ±8%, ±10%, ±15%, ±20%, ±25%, or as otherwise known in the art. "Substantially" refers to more than 66%, 75%, 80%, 90%, 95%, or, depending on the context within which the term substantially appears, value otherwise as known in the art.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. An implantable medical device comprising:
    an electromechanical substrate;
    a pressure sensor disposed on the electromechanical substrate;
    a flexible outer membrane surrounding the pressure sensor and forming a package, wherein the package is defined by a volume that contains the pressure sensor, wherein the flexible outer membrane comprises a poly (p-xylylene) material and has a shape and a thickness, wherein the shape comprises corrugations, and wherein the thickness is between 1 µm and 10 µm; and
    a hydrophobic liquid disposed in the volume and in contact with the pressure sensor and the flexible outer membrane, wherein the hydrophobic liquid has a kinematic viscosity between 5,000 cSt and 100,000 cSt.

2. The implantable medical device of claim 1, wherein the poly(p-xylylene) material comprises parylene.

3. The implantable medical device of claim 1, wherein the hydrophobic liquid comprises one or more of: a silicone oil or a vegetable oil.

4. The implantable medical device of claim 1, wherein the flexible outer membrane and the hydrophobic liquid form the package that contains the pressure sensor and the electromechanical substrate.

5. The implantable medical device of claim 1, wherein the flexible outer membrane and the hydrophobic liquid form the package, and wherein a surface of the package has a curvature predefined based on a temperature differential.

6. The implantable medical device of claim 5, wherein the temperature differential is between a temperature of a manufacturing environment and a temperature of an operational environment, wherein the curvature is concave based on the temperature of the operational environment being larger than the temperature of the manufacturing environment.

7. The implantable medical device of claim 5, wherein the temperature differential is between a temperature of a manufacturing environment and a temperature of an operational environment, wherein the curvature is convex based on the temperature of the operational environment being smaller than the temperature of the manufacturing environment.

8. The implantable medical device of claim 5, further comprising a first post disposed on the pressure sensor, and wherein the curvature is based on the first post.

9. The implantable medical device of claim 1, wherein the thickness is equal to or larger than 1 μm and is less than 5 μm.

10. The implantable medical device of claim 1, wherein the kinematic viscosity of the hydrophobic liquid falls within a kinematic viscosity range, wherein the kinematic viscosity range is predefined based on a time delay.

11. The implantable medical device of claim 10, wherein the kinematic viscosity range is between 20,000 cSt and 100,000 cSt.

12. The implantable medical device of claim 10, wherein the pressure sensor comprises a pressure port in contact with the hydrophobic liquid.

13. The implantable medical device of claim 1, further comprising a rigid structure that contains the pressure sensor, the flexible outer membrane, and the hydrophobic liquid, and wherein an outer surface of the rigid structure comprises holes.

14. The implantable medical device of claim 1, further comprising:
a post attached to the pressure sensor, wherein the flexible outer membrane is biocompatible, and wherein a surface of the flexible outer membrane has a curvature defined based on the post and the kinematic viscosity of the hydrophobic liquid.

15. The implantable medical device of claim 1, wherein the pressure sensor comprises a pressure port.

16. The implantable medical device of claim 1, further comprising a first post disposed on the pressure sensor and a second post disposed on the pressure sensor, and wherein the first post and the second posts are of different lengths, and wherein the first post, the second post, and a portion of the flexible outer membrane form a curvature.

17. The implantable medical device of claim 1, further comprising a first post disposed on the pressure sensor and a second post disposed on the electromechanical substrate, and wherein the first post, the second post, and a portion of the flexible outer membrane form a curvature.

18. The implantable medical device of claim 1, wherein the corrugations are configured to change upon implantation of the implantable medical device in an operational environment, and wherein the corrugations are induced in the poly(p-xylylene) material prior to the implantation.

* * * * *